(12) United States Patent
Knowlton

(10) Patent No.: US 6,749,624 B2
(45) Date of Patent: *Jun. 15, 2004

(54) FLUID DELIVERY APPARATUS

(76) Inventor: Edward W. Knowlton, 5478 Blackhawk Dr., Danville, CA (US) 94506

(*) Notice: Subject to any disclaimer, the term of this patent is extended or adjusted under 35 U.S.C. 154(b) by 0 days.

This patent is subject to a terminal disclaimer.

(21) Appl. No.: 10/026,870

(22) Filed: Dec. 20, 2001

(65) Prior Publication Data

US 2002/0049483 A1 Apr. 25, 2002

Related U.S. Application Data

(63) Continuation of application No. 09/337,015, filed on Jun. 30, 1999, now Pat. No. 6,350,276, which is a continuation-in-part of application No. 08/583,815, filed on Jan. 5, 1996, now Pat. No. 6,241,753, and a continuation-in-part of application No. 08/827,237, filed on Mar. 28, 1997, and a continuation-in-part of application No. 08/914,681, filed on Aug. 19, 1997, now Pat. No. 5,919,219, and a continuation-in-part of application No. 08/942,274, filed on Sep. 30, 1997.

(51) Int. Cl.$^7$ ................................ A61F 7/00; A61F 2/00
(52) U.S. Cl. ......................... 607/104; 606/33; 606/41; 607/101
(58) Field of Search ..................... 606/2, 9, 10, 11, 606/13, 16, 41, 42, 45, 46, 48, 49, 50, 32, 33; 607/88, 89, 101–102, 104, 108–112

(56) References Cited

U.S. PATENT DOCUMENTS

| 3,831,604 A | 8/1974 | Neefe ..................... 128/260 |
| 4,074,718 A | 2/1978 | Morrison ............ 128/303.14 |

(List continued on next page.)

FOREIGN PATENT DOCUMENTS

| DE | 1 949 534 | 4/1970 | |
| DE | 31 21 683 | 12/1982 | |
| EP | 0 395 307 A2 | 10/1990 | ........... A61B/17/36 |
| EP | 0 519 415 | 12/1992 | |
| FR | 2 609 245 | 7/1988 | |
| NZ | 266678 | 12/1997 | |
| WO | 92/19414 | 11/1992 | |
| WO | 93/13816 | 7/1993 | |
| WO | 94/26228 | 11/1994 | |
| WO | 96/27240 | 9/1996 | |
| WO | 96/27327 | 9/1996 | |
| WO | 96/32051 | 10/1996 | |
| WO | 96/34568 | 11/1996 | |
| WO | 96/39914 | 12/1996 | |
| WO | 97/18765 | 5/1997 | |
| WO | 97/18768 | 5/1997 | |
| WO | 68/03117 | 1/1998 | |
| WO | 98/03220 | 1/1998 | |
| WO | 98 05286 | 2/1998 | ........... A61H/7/00 |
| WO | 99 08614 | 2/1999 | ........... A61B/17/39 |
| WO | 02/26147 | 4/2002 | ........... A61B/18/14 |

OTHER PUBLICATIONS

Allain, et al. "Isometric Tensions Developed During the Hydrothermal Swelling of Rat Skin", Connective Tissue Research, vol 7, pp. 697–701, (1990).

(List continued on next page.)

Primary Examiner—Roy D. Gibson
(74) Attorney, Agent, or Firm—Paul Davis; Heller Ehrman White & McAuliffe

(57) ABSTRACT

A fluid delivery apparatus for introducing a fluid cooling media to a skin surface includes a template with a skin interface surface. An energy delivery device is coupled to the template. A fluid cooling media introduction member is coupled to the template. Resources controllably deliver energy from the energy delivery device to the skin surface. In a related embodiment, the resources are configured to controllably deliver the flowable cooling media to the introduction member. In another embodiment, a sensor is coupled to the resources and to the skin surface.

71 Claims, 26 Drawing Sheets-

U.S. PATENT DOCUMENTS

| | | | |
|---|---|---|---|
| 4,140,130 A | 2/1979 | Storm, III | 128/404 |
| 4,164,226 A | 8/1979 | Tapper | 128/419 R |
| 4,290,435 A | 9/1981 | Waggott | 128/800 |
| 4,343,301 A | 8/1982 | Indech | 128/24 |
| 4,346,715 A | 8/1982 | Gammell | 128/422 |
| 4,375,220 A | 3/1983 | Matvias | 128/804 |
| 4,381,007 A | 4/1983 | Doss | 128/303.1 |
| 4,441,486 A | 4/1984 | Pounds | 128/24 |
| 4,545,368 A | 10/1985 | Rand et al. | 128/1.3 |
| 4,556,070 A | 12/1985 | Vaguine et al. | |
| 4,633,875 A | 1/1987 | Turner | |
| 4,676,258 A | 6/1987 | Inokuchi et al. | 128/804 |
| 4,709,701 A | 12/1987 | Weber | 128/422 |
| 4,756,310 A | 7/1988 | Bitterly | 128/400 |
| RE32,849 E | 1/1989 | Wei et al. | 204/192.27 |
| 4,881,543 A | 11/1989 | Trembly et al. | 128/303.1 |
| 4,887,614 A | 12/1989 | Shirakami et al. | 128/798 |
| 4,889,122 A | 12/1989 | Watmough et al. | 128/399 |
| 4,944,302 A | 7/1990 | Hernandez et al. | 128/798 |
| 4,957,480 A | 9/1990 | Morenings | 604/20 |
| 4,962,761 A | 10/1990 | Golden | 128/400 |
| 4,976,709 A | 12/1990 | Sand | 606/5 |
| 5,003,991 A | 4/1991 | Takayama et al. | 128/784 |
| 5,133,351 A | 7/1992 | Masaki | 128/419 R |
| 5,143,063 A | 9/1992 | Fellner | 128/399 |
| 5,186,181 A | 2/1993 | Franconi et al. | 128/804 |
| 5,190,517 A | 3/1993 | Zieve et al. | 604/22 |
| 5,230,334 A | 7/1993 | Klopotek | 128/399 |
| 5,231,997 A | 8/1993 | Kikuchi et al. | |
| 5,249,575 A | 10/1993 | DiMino et al. | 607/150 |
| 5,282,797 A | 2/1994 | Chess | 606/9 |
| 5,304,169 A | 4/1994 | Sand | 606/5 |
| 5,315,994 A | 5/1994 | Guibert et al. | 607/101 |
| 5,334,193 A | 8/1994 | Nardella | 606/41 |
| 5,342,357 A | 8/1994 | Nardella | 606/40 |
| 5,348,554 A | 9/1994 | Imran et al. | 606/41 |
| 5,366,443 A | 11/1994 | Eggers et al. | |
| 5,370,642 A | 12/1994 | Keller | 606/9 |
| 5,374,265 A | 12/1994 | Sand | 606/5 |
| 5,423,807 A | 6/1995 | Milder | 606/20 |
| 5,423,811 A | 6/1995 | Imran et al. | 606/41 |
| 5,437,662 A | 8/1995 | Nardella | 606/40 |
| 5,458,596 A | 10/1995 | Lax et al. | 606/31 |
| 5,462,521 A | 10/1995 | Brucker et al. | 604/20 |
| 5,464,436 A | 11/1995 | Smith | 607/89 |
| 5,496,312 A | 3/1996 | Klicek | |
| 5,500,012 A * | 3/1996 | Brucker et al. | 607/122 |
| 5,507,790 A | 4/1996 | Weiss | |
| 5,556,377 A * | 9/1996 | Rosen et al. | 604/22 |
| 5,569,242 A | 10/1996 | Lax et al. | 606/42 |
| 5,643,334 A | 7/1997 | Eckhouse et al. | 607/88 |
| 5,655,547 A | 8/1997 | Karni | 128/898 |
| 5,660,836 A | 8/1997 | Knowlton | 424/400 |
| 5,681,282 A | 10/1997 | Eggers et al. | |
| 5,683,366 A | 11/1997 | Eggers et al. | |
| 5,692,058 A | 11/1997 | Eggers et al. | |
| 5,693,045 A | 12/1997 | Eggers | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,755,753 A | 5/1998 | Knowlton | 607/98 |
| 5,769,879 A | 6/1998 | Richards et al. | 607/101 |
| 5,775,338 A | 7/1998 | Hastings | 128/898 |
| 5,776,092 A * | 7/1998 | Farin et al. | 604/22 |
| 5,776,175 A | 7/1998 | Eckhouse et al. | 607/100 |
| 5,814,040 A | 9/1998 | Nelson et al. | 606/9 |
| 5,833,612 A | 11/1998 | Eckhouse et al. | 600/476 |
| 5,836,999 A | 11/1998 | Eckhouse et al. | 607/88 |
| 5,964,749 A | 10/1999 | Eckhouse et al. | 606/9 |
| 5,970,983 A | 10/1999 | Karni et al. | 128/898 |
| 5,979,454 A | 11/1999 | Anvari et al. | 128/898 |
| 6,139,569 A | 10/2000 | Ingle et al. | 607/104 |
| 6,162,212 A | 12/2000 | Kreindel et al. | 606/9 |
| 6,171,301 B1 | 1/2001 | Nelson et al. | 606/9 |
| 6,248,103 B1 | 6/2001 | Tannenbaum et al. | 606/9 |
| 6,387,089 B1 | 5/2002 | Kreindel et al. | 606/9 |

OTHER PUBLICATIONS

Danielson, C. "Age–Related thermal stability and susceptibility to proteolysis of rat bone collagen", . . . chem, Great Britain, pp. 697–701, (1990).

Danielson, C. "Thermal stability of reconstituted collagin fibrils, shrinkage characteristics upon in vitro maturation", Mechanisms of Ageing and Development, vol 15, pp. 269–278, (1981).

Kronick, et al. "The locations of collagens with different thermal stabilities in fibrils of bovine recticular dermis". Connective Tissue Research, vol. 18, pp. 123–134, (1988).

Mainster, M.A. "Opthalmic applications of infrared lasers—thermal considerations", Visual Sci., pp. 414–420, Apr. 1979.

Pearce, et al. "Kinetic models of laser–tissue fusion processes", ISA, paper #93–044, pp. 355–360, (1993).

Adrian, R. M. Treatment of Facial Telangiectasia Using the VersePulse® Variable Pulse Width Frequency Doubled Neodymium:YAG Laser: A Case Report.

Chess, C.; Chess. Q. "Cool Laser Optics Treatment of Large Telangiestasia of the Lower Extremities." *J. Dermatol Surg Oncol.* 1993; 19:74–80.

Coulson, W. F. et al. "Nonablative Laser Treatment of Facial Rhytides: Animal Study." Abstract for BiOS '98 Symposium Conference: bo05—Cutaneous Applications of Lasers, Jan. 24–30, 1998, San Jose, CA.

Kincade, K. "Demand for Laser Resurfacing Soars: Quicker Healing, Less Risk of Scarring" *Dermatology Times.* 1995. 16(10).

Fitzpatrick, R. "Treatment of Wrinkles with the UltraPulse $CO_2$ Laser."

Laser Aesthetics, Inc. "The Cool Touch Laser." Brochure.

Laser Aesthetics, Inc. "Cool Touch Model 130 Technical Specifications." Brochure.

National Health Communications, Inc. "New Laser Eliminates 'Lipstick Bleed'" Press Release Jul. 1993.

\* cited by examiner

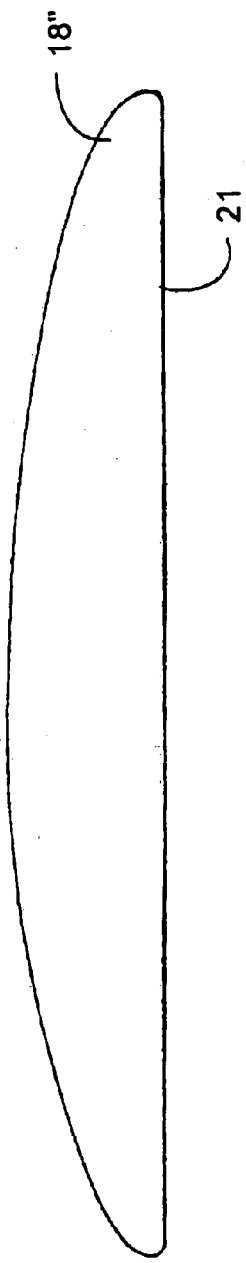
FIG. 19A
FIG. 19B

FLUID DELIVERY APPARATUS

CROSS REFERENCE TO RELATED APPLICATION

This application is a continuation of U.S. patent application Ser. No. 09/337,015, filed Jun. 30, 1999 U.S. Pat. No. 6,350,276 which is a continuation-in-part of U.S. patent application Ser. No. 08/583,815, filed Jan. 5, 1996 U.S. Pat. No. 6,241,753, a continuation-in-part of U.S. patent application Ser. No. 08/827,237, filed Mar. 28, 1997, a continuation-in-part of U.S. patent application Ser. No. 08/914,681, filed Aug. 19, 1997 U.S. Pat. No. 5,919,219, and a continuation-in-part of U.S. patent application Ser. No. 08/942,274 filed Sep. 30, 1997.

BACKGROUND OF THE INVENTION

1. Field of the Invention

This invention relates to an apparatus for modifying skin surfaces and underlying tissue and more particularly to an apparatus for modifying skin surfaces and underlying tissue via the delivery of energy and fluid.

2. Description of Related Art

The correction of a deformity or the esthetic enhancement of a soft tissue structure is determined by the balance of the skin envelope as the container and soft tissue volume as the contents of the container. An appropriate balance between these two components is essential in achieving a successful outcome. Most plastic surgery procedures are based upon the resection or addition of a soft tissue filler with a concomitant modification of the skin envelope. For example, a breast that has three dimensional symmetry with the opposite breast must take into account both the volume of the soft tissue and the surface area of the breast envelope that is required as a container of the tissue. Breast reconstruction after mastectomy typically involves the insertion of a soft tissue replacement for the removed breast tissue. Either an implant or a tissue flap from the patient is used as a soft tissue replacement. Expansion of the breast skin envelope is also required and is achieved with a medical device called a breast expander. While most reconstructive procedures usually involve the addition of a soft tissue filler with the expansion of the skin envelope, many esthetic procedures involve the reduction of the soft tissue contents with or without a reduction in the skin envelope. Reduction in the volume of the soft tissue contents without a concomitant reduction in the skin envelope may lead to a relative excess of the skin envelope. The relative excess will be visualized as loose skin or elastosis. An example of esthetic enhancement is a procedure called breast reduction. This is performed in women who require reduction in the size of their breasts to alleviate shoulder, neck and back symptoms. Breast tissue is resected to reduce volume but also requires a reduction in the breast skin envelope with extensive surgical incisions. Without reduction of the skin envelope of the breast, severe ptosis (droopiness) of the breast will occur.

Another example is liposuction which may aggravate elastosis because the soft tissue content is reduced without reduction in the surface area of the skin envelope. The degree of esthetic contour reduction is limited by the preexisting looseness of the skin envelope. Typically, liposuction involves the removal of subcutaneous fat through a suction cannula inserted through the skin surface. Excess suctioning of fat will aggravate any preexisting elastosis. Any other modality that reduces subcutaneous fat through dieting or ablation of fat cells is likely to aggravate a preexisting elastosis if a concomitant reduction of the skin envelope does not occur. This is especially true in the hip and thigh area where a condition called "cellulite" is due to a preexisting looseness of skin. Many patients have a more severe looseness of skin in the hip and thigh area that would be aggravated by any fat removal. Skin tightening procedures that involve large surgical incisions result in severe scarring to the thigh and hip area that are a poor tradeoff to any esthetic contour reduction.

There is a need for a method and apparatus to achieve skin tightening without major surgical intervention. There is a further need for a method and apparatus to achieve skin tightening by the controlled remodeling of collagen in the skin and underlying fibrous partitions of the subcutaneous fat. Still a further need exists to tighten a skin envelop with minimal skin or underlying subcutaneous tissue cell necrosis. Yet another need exists to provide a method and apparatus for the controlled remodeling of collagen in tandem with subcutaneous fat ablation in which a net tightening of the skin envelope occurs with an esthetic contour reduction.

SUMMARY OF THE INVENTION

Accordingly, an object of the invention is to provide a method and apparatus to tighten skin.

Another object of the invention is to provide a method and apparatus to tighten skin without major surgical intervention.

Yet another object of the invention is to provide a method and apparatus to tighten skin with controlled remodeling of collagen.

A further object of the invention is to provide a method and apparatus that delivers a mechanical force and electromagnetic energy to a tissue site to change a skin surface.

A further object of the invention is to provide a method and apparatus that delivers a mechanical force and electromagnetic energy to a tissue site to change the contour of a soft tissue structure.

These and other objects of the invention are achieved in a fluid delivery apparatus for introducing a flowable cooling media to a skin surface. The apparatus includes a template with a skin interface surface. An energy delivery device is coupled to the template. A flowable cooling media introduction member is coupled to the template. Resources controllably deliver energy from the energy delivery device to the skin surface. In a related embodiment, the resources are configured to controllably deliver the flowable cooling media to the introduction member. In another embodiment, a sensor is coupled to the resources and to the skin surface.

BRIEF DESCRIPTION OF THE FIGURES

FIGS. 19a and 19b are later views illustrating geometric embodiments of an RF electrode configured to reduce edge effects

DETAILED DESCRIPTION

Figure 1:
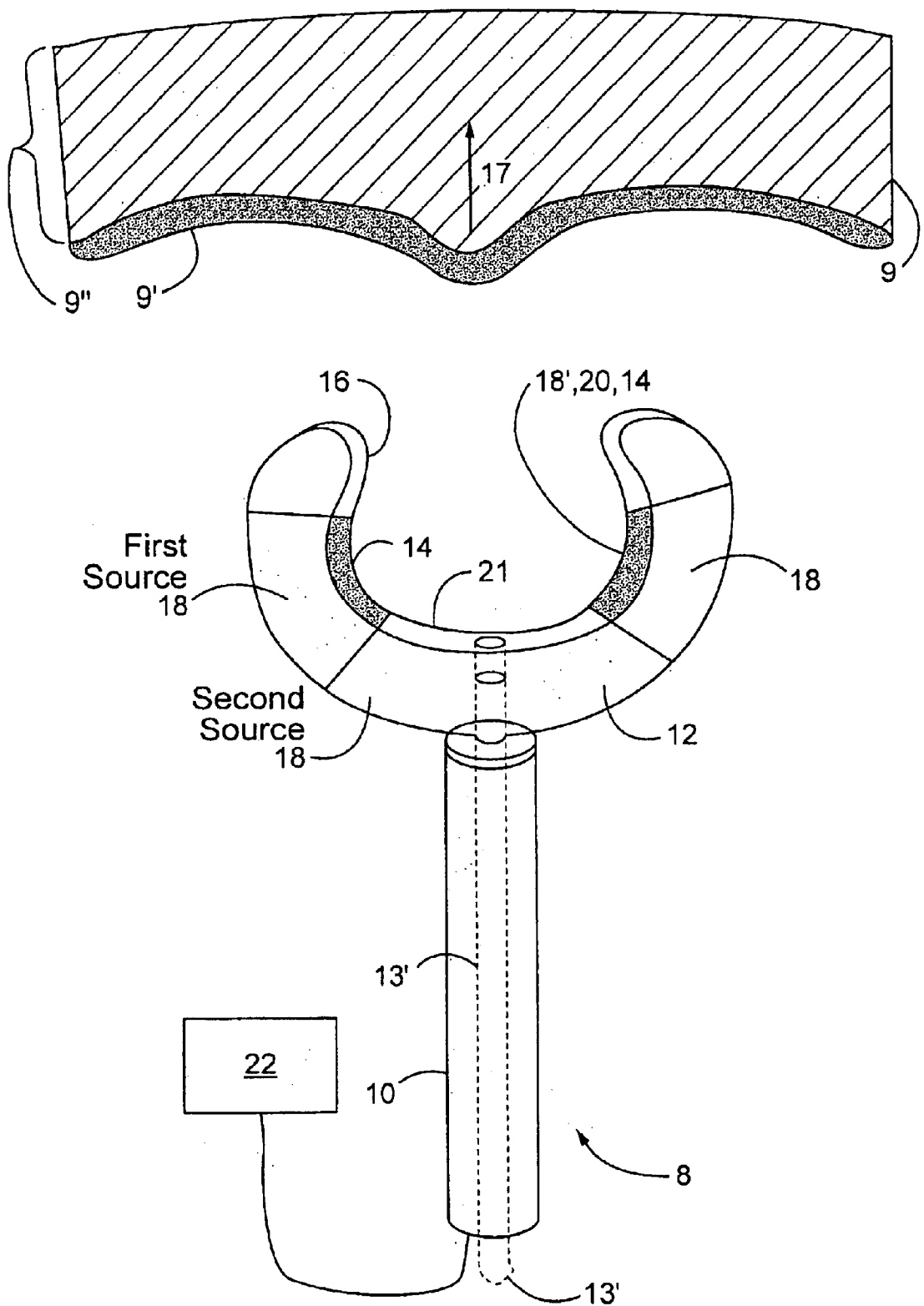
FIG. 1 is a perspective view of the apparatus of the present invention.

FIG. 1 depicts an apparatus 8 to modify a tissue structure 9 or tissue 9 (including an underlying tissue layer 9" and/or a surface or skin layer 9'). Tissue 9 can include skin tissue or any collagen containing tissue and underlying tissue 9" can include dermal and subdermal layers including collagen containing underlying tissue. In various embodiments, apparatus 8 can have one or more of the following features: i) feedback control of energy delivery and applied force and other parameters discussed herein ii) cooled energy delivery devices, iii) delivery of cooling fluid to tissue site and/or energy devices iv) contact sensing of electrodes, v) control of energy delivery and applied force via the use of a database of combinations of energy, force, pressure, etc including direction, rates and total amounts delivered over time, the data base can alone or in combination with feedback control.

Figure 2A:
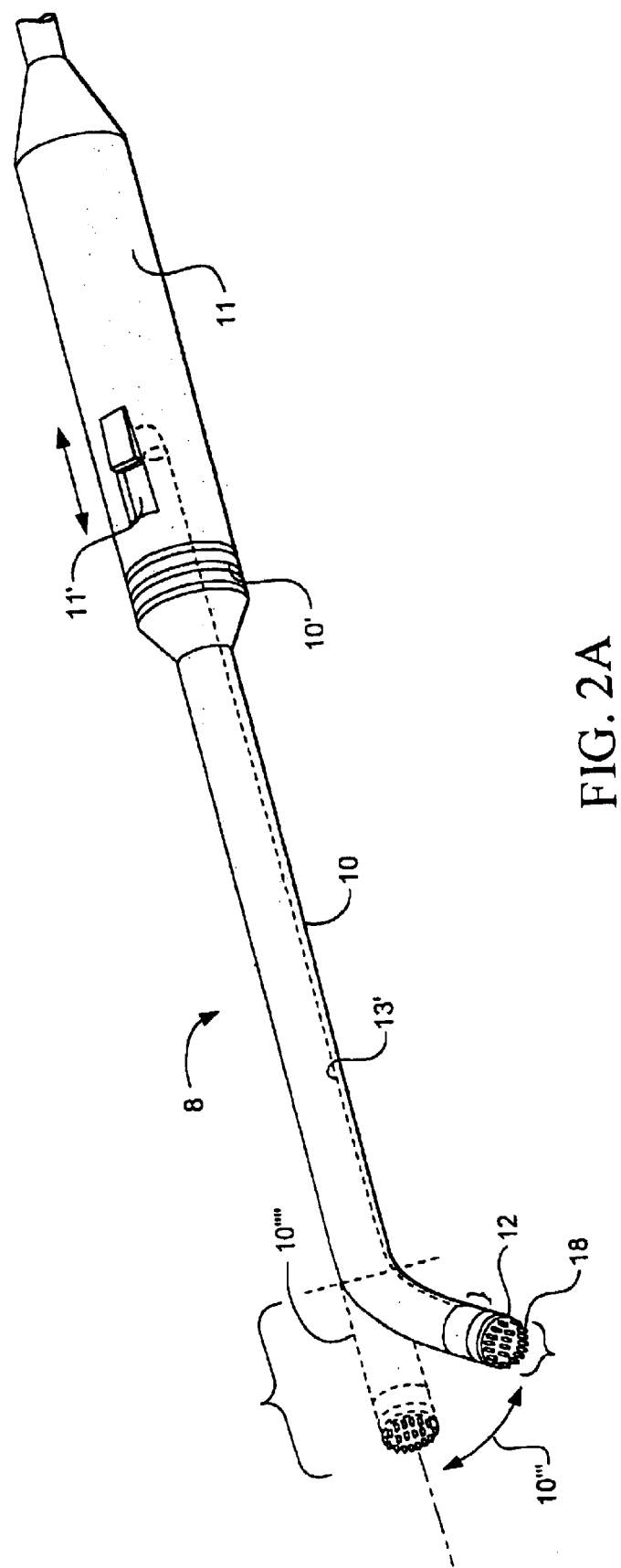
FIG. 2a is a lateral perspective view of the apparatus of FIG. 1 illustrating the introducer, template and energy delivery device.
Figure 2B:
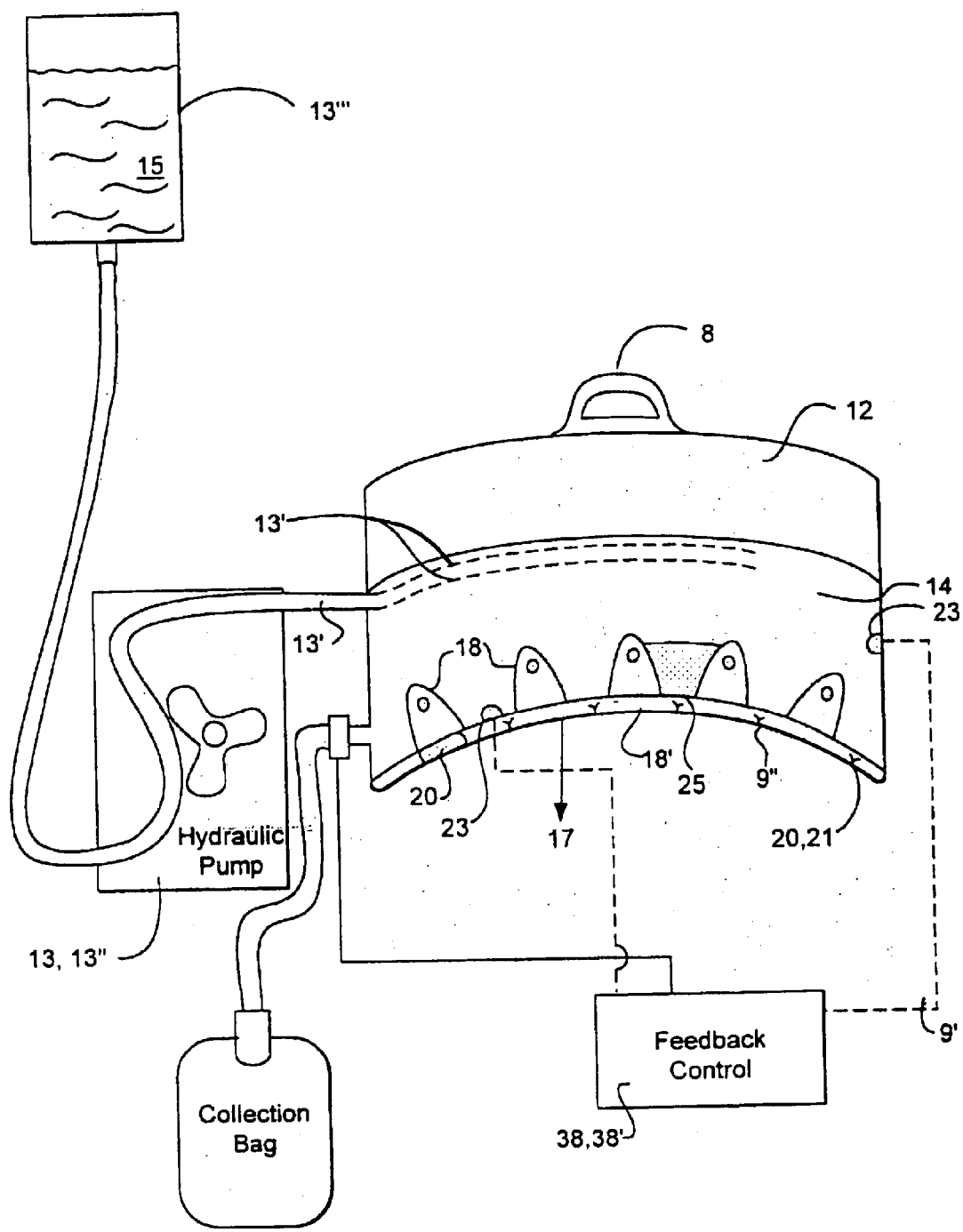
FIG. 2b is a lateral perspective view of the apparatus of FIG. 1 illustrating the use of a fluid delivery device.

Referring now to FIGS. 1, 2a and 2b, apparatus 8 includes an introducer 10 with proximal and distal ends 10' and 10". Introducer 10 is coupled at its distal end 10" to a template 12 which in turn includes a soft tissue mechanical force application surface 14 and a receiving opening 16 to receive a body structure. Mechanical force application surface 14 is configured to receive the body structure and apply force to soft tissue in the body structure, resulting in the application of a force 17 to that structure including its surface and underlying tissue.

Introducer 10 may have one or more lumens 13' that extend the full length of the introducer or only a portion thereof. These lumens may be used as paths for the delivery of fluids and gases, as well as providing channels for cables, catheters, guide wires, pull wires, insulated wires, optical fibers, and viewing devices/scopes. In one embodiment, the introducer can be a multi-lumen catheter, as is well known to those skilled in the art. In another embodiment, introducer 10 can include or otherwise be coupled to a viewing device such as endoscope, viewing scopes and the like.

In various embodiments, apparatus 8 can include a handpiece 11 coupled to introducer 10. Handpiece 11 can include a deflection mechanism 11' such as a pull wire or other mechanism known in the art. Deflection mechanism 11' can be used to deflect the distal end 10" of introducer 10 including template 12 by an angle 10''' relative to a lateral axis 10'''' of introducer 10. In various embodiments angle 10''' can be an acute angle (e.g <90E) with specific embodiments of 60, 45 or 30E.

An energy delivery device 18 is coupled to template 12. Energy delivery device 18 is configured to deliver energy to template 12 to form a template energy delivery surface 20 at an interior of template 12. Energy delivery surface 20 contacts the skin or other tissue at a tissue interface 21. In various embodiments, one or more energy delivery devices 18 may deliver energy to template 12 and energy delivery surface 20. An energy source 22 (described herein) is coupled to energy delivery device 18 and/or energy delivery surface 20. Energy delivery device 18 and energy source 22 may be a single integral unit or each can be separate.

Referring now to FIG. 2b, a fluid delivery device 13 can be coupled to introducer 10 and/or template 12 including energy delivery device 18. Fluid delivery device 13 (also called cooling device 13) serves to deliver fluid to tissue interface 21 and surrounding tissue to prevent or otherwise reduce thermal damage of the skin surface with the topical application of energy. In various embodiments, fluid delivery device 13 can include one or more lumens 13' which can be the same or otherwise continuous (e.g. fluidically coupled) with lumen 13' in introducer 10 and template 12.

Lumens 13' can be fluidically coupled to a pressure source 13" and fluid reservoir 13'". Fluid delivery device 13 can also be coupled to a control system described herein. In various embodiments, pressure source 13" can be a pump (such as a peristaltic pump) or a tank or other source of pressurized inert gas (e.g. nitrogen, helium and the like).

Fluid delivery device 13 is configured to deliver a heat transfer media 15 (also called a cooling media 15, flowable media 15 or fluid 15) to tissue interface 21, that serves to dissipate sufficient heat from the skin and underlying tissue at or near tissue interface 21 during the delivery of energy at or near this site so as to prevent or reduce thermal damage including burning and blistering. Similarly, fluid delivery device 13 may also deliver fluid 15 to and dissipate heat from energy delivery device 18 and/or template 12 to achieve a similar result. In various embodiments, introducer 10, including lumens 13' can serve as a cooling media introduction member 10 for heat transfer media 15.

Fluid 15 serves as a heat transfer medium and its composition and physical properties can be configured to optimize its ability to dissipate heat. Desirable physical properties of fluid 15 include, but are not limited to, a high heat capacity (e.g. specific heat) and a high thermal conductivity (e.g. conduction coefficient) both of which can be comparable to liquid water in various embodiments or enhanced by the addition of chemical additives known in the art. In other embodiments, fluid 15 may also serve to conduct RF energy and therefore have good electrical conductivity. Fluid 15 can be selected from a variety of fluids including, but not limited to water, saline solution (or other salt aqueous salt solutions), alcohol (ethyl or methyl), ethylene glycol or a combination thereof. Also, fluid 15 can be in a liquid or gaseous state, or may exist in two or more phases and may undergo a phase change as part of its cooling function, such as melting or evaporation (whereby heat is absorbed by the fluid as a latent heat of fusion or evaporation). In a specific embodiment, fluid 15 can be a liquid at or near its saturation temperature. In another embodiment, fluid 15 can be a gas which undergoes a rapid expansion resulting in a joule Thompson cooling of one or more of the following: fluid 15, tissue interface 21, energy delivery device 18 and energy delivery surface 20. In various embodiments, fluid 15 can be cooled to over a range of temperatures including but not limited to 32 to 98° F. In other embodiments fluid 15 can be configured to be cooled to cryogenic temperatures in a range including but not limited to 32 to −100° F. Fluid or heat transfer media 15 can be cooled by a variety of mechanisms, including but not limited to, conductive cooling, convective cooling (force and unforced), radiative cooling, evaporative cooling, melt cooling and ebullient cooling. Ebullient cooling involves the use of a liquid heat transfer liquid at or near saturation temperature. In various embodiments fluid 15 can also be an electrolytic fluid used to conduct or delivery RF energy to or in tissue and/or reduce impedance of tissue.

In other embodiments, thermal damage to skin 9' and underlying tissue 9" can be reduced or prevented through the use of a reverse thermal gradient device 25. Reverse thermal gradient device 25 can be positioned at or thermally coupled to template 12, mechanical force application surface 14 or energy delivery device 18. Suitable reverse thermal gradient devices 25 include but are not limited to peltier effect devices known in the art.

The delivery of cooling fluid 15 by fluid delivery device 13, energy (e.g. heat) by energy delivery device 18 and force (e.g. pressure) by force applications surface 14 can be regulated separately or in combination by a feedback control system described herein. Inputs parameters to the feedback control system 54 can include, but are not limited to temperature, impedance and pressure of the tissue interface 21 energy delivery device 18 (including surface 18') and underlying structure, separately or in combination. The sequence of cooling and heating delivered to tissue interface 21 is controllable to prevent or reduce burning and other thermal damage to tissue.

Different cooling and heating control algorithms can be employed in different combinations of continuous and discontinuous modes of application. Specific control algorithms that can be employed in a control system described herein include proportional (P), proportional-integral (PI) and proportional-integral-derivative algorithms (PID) the like, all well known in the art. These algorithms can use one or more input variables described herein and have their proportional, integral and derivative gains tuned to the specific combination of input variables. The control algorithms can be run either in an analog or digital mode using hardware described herein. Temporal modes of delivery of cooling and energy to tissue interface 21 include, but are not limited to fixed rate continuous, variable rate continuous, fixed rate pulsed, variable rate pulsed and variable amount pulsing. Example delivery modes include the continuous application of the cooling means in which the flow rate is varied and application of the power source is pulsed or continuous i.e., the application of power can be applied in a pulsed fashion with continuous cooling in which the flow rate of cooling solution and the rate of RF energy pulsing (at a set power level) is varied as a function of surface monitoring of tissue interface 21. Pulsing of the cooling medium 15 flow rate may be either a constant or variable rate. A pulsed or intermittent application of cooling in which the frequency of pulsing is determined by surface monitors can also be combined with the application of a continuous or pulsed energy source. For instance, cooling is applied as an intermittent spraying of a cryogen solution with a continuous application of RF energy. Even the amount of a single pulse of the cooling medium can be varied (variable amount pulsing). Any liquid, such as a cryogen (e.g. liquid nitrogen) that quickly evaporates with heat, can be applied in this fashion. Another example of variable pulsing is the application of a constant rate of RF pulsing at a variable power level that is feedback controlled. Cooling can also be varied by pulsing the flow rate of continuous cooling. More complicated algorithms involve the use of variable sequences of both cooling and heating. Less complicated algorithms involve a variable component with a fixed component of heating or cooling. The least complicated algorithm involves the use of a data base that may not be feedback controlled, in which certain fixed or non variable combinations of heating and cooling are allowed to initiate a treatment cycle.

Template 12 can deliver both electromagnetic energy and mechanical force to the selected tissue or anatomical structure 9. Suitable anatomical structures 9 include, but are not limited to, hips, buttocks, thighs, calves, knees, angles, feet, perineum, the abdomen, chest, back flanks, waistline, legs, arms, legs, arms, wrists, upper arms, axilla, elbows, eyelids, face, neck, ears, nose, lips, checks, forehead, hands, breasts and the like. In various embodiments, tissue structure 9 includes any collagen containing tissue structure.

Mechanical force application surface 14 can apply pressure, suction, adhesive forces and the like in order to create an extension or compression of the soft tissue structure and/or the skin surface. One or more energy delivery devices 18 can form an energy delivery surface 20 in template 12. In various embodiments, energy delivery surface 20 can be the same size as force application surface 14 or it can be a smaller area.

A variety of mechanical forces can be applied to tissue using apparatus 8 and force application surface 14, including but not limited to, the following: (i) pressure, (ii) expansion, (iii) stretching, (iv) extension, (v) prolongation, or (vi) lengthening. The pressure force can be a positive pressure or a negative pressure. Positive pressure provides a compression of collagen containing tissue, with converging and diverging force vectors, while negative pressure creates an extension of collagen containing tissue with converging and diverging vectors. In various embodiments, the force 17 applied by force application surface 14 to tissue interface 21 is monitored and used as an input parameter (by sensors 23 described herein) as well as feedback controlled (by means described herein) so as to perform or facilitate one or more of the following functions: (i) minimize and/or prevent burning and other thermal tissue damage; (ii) serve as a therapeutic modality to increase or decrease the delivery of thermal energy and mechanical force to the intended treatment site. In a preferred embodiment, the applied force 17 measured and monitored as described, is a pressure (e.g. force per unit tissue surface area) or otherwise expressed as such. In bipolar electrode applications describe herein, the force 17 applied by force application surface 14 should be limited to that amount necessary to achieve contact with skin.

Suitable sensors 23 that can that can be used to measure applied force or pressure to tissue include, but are not limited to strain gauges which can be made out of silicon and micro machined using techniques well known in the art. Suitable pressure sensors include the NPH series TO-8 Packaged Silicon Pressure Sensor manufactured by Lucas NovaSensor7.

In various embodiments, energy delivery device 18 can be configured to operate within the following parameters: (i) provides a controlled delivery of electromagnetic energy to the skin surface that does not exceed, 1,000 joules/cm2, or 10 joules/sec/cm2; (ii) provides a controlled delivery of electromagnetic energy to the skin surface not exceeding 600 joules/cm2 during a single treatment session (during a twenty-four hour period); provides a controlled delivery of electromagnetic energy to the skin surface not exceeding 200 joules/cm2 during a single treatment session, or not exceeding 10 joules/sec/cm2; (iii) operates in an impedance range at the skin surface of, 70 ohms cm2 (measured at a frequency of 88 Hz) to 40 Kohms cm2 (measured at a frequency of 10 KHz); (iv) provides a controlled delivery of electromagnetic energy to operate in a range of skin thermal conductivities (at or near the skin surface) of 0.20 to 1.2 k (where $k=1*[W/(m° C.)]$); operates in a range of compression forces applied to the skin surface and/or the underlying soft tissue anatomical structure not exceeding 400 mmHg, not exceeding 300 mm, not exceeding 200 mmHg or not exceeding 100 mmHg.

Suitable energy sources 22 that may be employed in one or more embodiments of the invention include, but are not limited to, the following: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, (xii) a microwave source or (xiii) a fluid jet.

For ease of discussion for the remainder of this application, the power source utilized is an RF source and energy delivery device 18 is one or more RF electrodes 18 also described as electrodes 18 having a surface 18'. However, all of the other herein mentioned power sources and energy delivery devices are equally applicable to apparatus 10.

Template 12 can apply both a mechanical force and deliver energy to do one or more of the following: (i) tighten the skin, (ii) smooth the surface of the skin, (iii) improve a compliance of the skin surface, (iv) improve a flexibility of the skin surface; and (v) provides cellular remodeling of collagen in soft tissue anatomical structures. Mechanical force application surface 14, (i) is at least partially conforming to the skin surface, (ii) may apply a substantially even pressure to the soft tissue anatomical structures and (iii) can apply a variable pressure to the skin surface and underlying soft tissue structures. The combined delivery of electromagnetic energy and a mechanical force is used to create a three-dimensional contouring of the soft tissue structure. The amount of mechanical force applied by mechanical force application surface 14 can be selectable to meet one or more of the following criteria: (i) sufficient to achieve a smoothing effect of the skin surface, (ii) can be less than the tensile strength of collagen in tissue and (iii) sufficient to create force vectors that cleave collagen cross-links to remodel collagen containing structures.

A sensor 23 is positioned at or adjacent energy delivery surface 20 and/or electrode 18 to monitor temperature, impedance (electrical), cooling media fluid flow and the like of tissue 9 of one or more of the following: tissue interface 21, tissue 11, or electrode 18. Suitable sensors 23 include impedance, thermal and flow measurement devices. Sensor 23 is used to control the delivery of energy and reduce the risk of cell necrosis at the surface of the skin as well and/or damage to underlying soft tissue structures. Sensor 23 is of conventional design, including but not limited to thermistors, thermocouples, resistive wires, and the like. A suitable thermal sensor 23 includes a T type thermocouple with copper constantene, J type, E type, K type, fiber optics, resistive wires, thermocouple IR detectors, and the like. Suitable flow sensors include ultrasonic, electromagnetic and aneometric (including thin and hot film varieties) as is well known in the art. In various embodiments, two or more temperature and impedance sensors 23 are placed on opposite sides or otherwise opposing geometric positions of electrode 18 or energy delivery surface 20.

Apparatus 8 can be configured to deliver sufficient energy and/or force to meet the specific energy requirements for disrupting and/or cleaving each type of molecular bond within the collagen matrix. Collagen crosslinks may be either intramolecular (hydrogen bond) or intermolecular (covalent and ionic bonds). Hydrogen bonds are disrupted by heat. Covalent bonds may be cleaved with the stress created from the hydrogen bond disruption and the application of an external mechanical force. Cleavage of ionic bonds may be achieved with an alternating electromagnetic force (as would be induced by an electromagnetic field such as an RF field) in addition to the application of an external mechanical force that is applied by template 12. The strength of a hydrogen bond is relatively weak and can be thermally disrupted without ablation of tissue. The in vitro thermal cleavage of the hydrogen bond crosslinks of tropocollagen can result in the molecular contraction of the triple helix up to one third of its original length. However, in vivo collagen exists in fibrils that have extensive intermolecular crosslinks that are covalent or ionic in nature. These covalent and ionic crosslinks are stronger and cannot be easily disrupted with heat alone. These intermolecular bonds are the main structural determinants of the collagen matrix strength and morphology. In vivo thermal disruption of intramolecular hydrogen bonds will not by itself result in a significant change in matrix morphology. As the intermolecular crosslinks are heat stable, cleavage may occur by a secondary process which can be the result of thermal disruption of intramolecular hydrogen bonds. In the non-polar region of the collagen fibril, intermolecular covalent bonds predominate (intramolecular covalent bonds are also present but are fewer in number).

Figure 3:
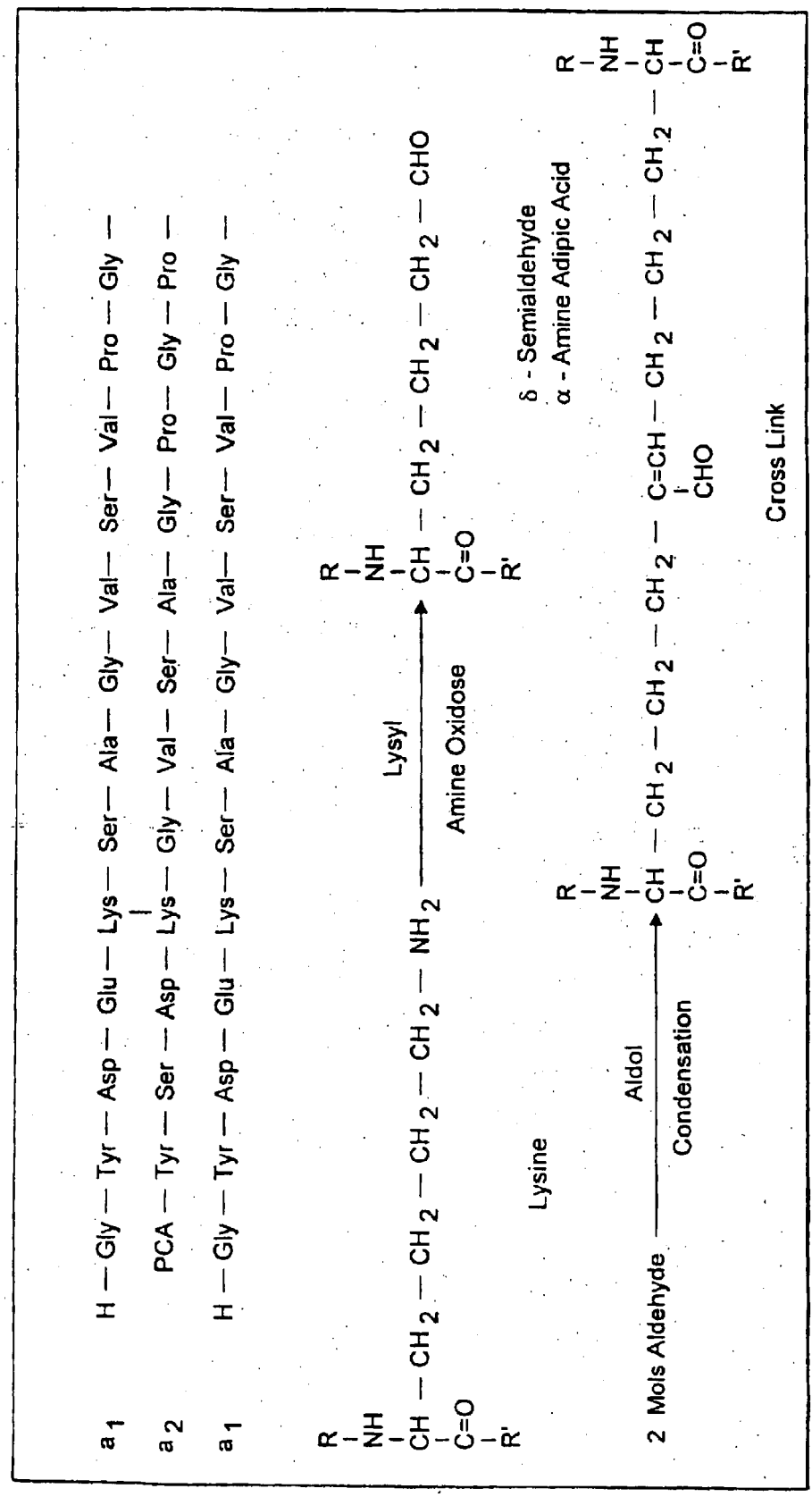
FIG. 3 illustrates intramolecular cross-linking of collagen.
Figure 4:
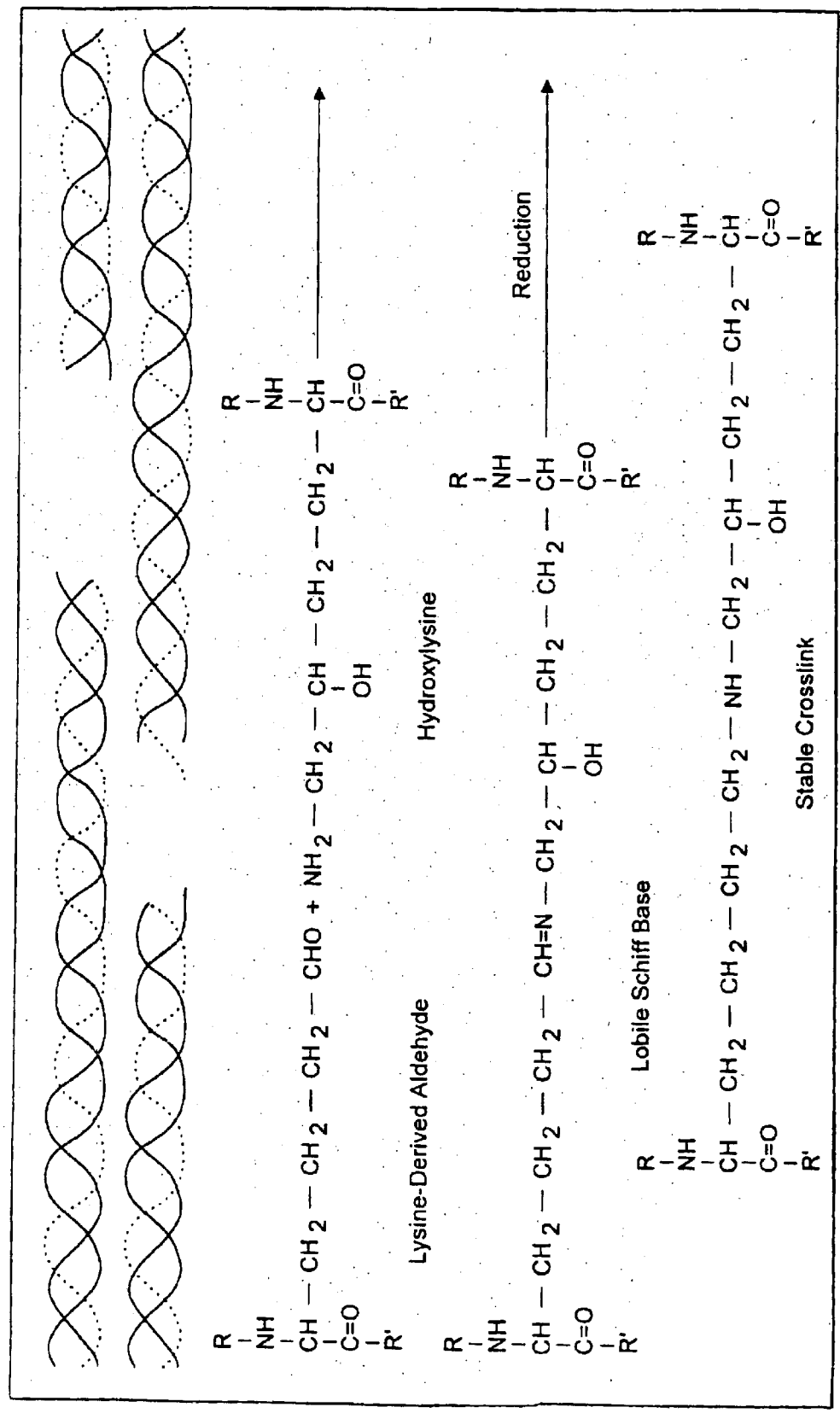
FIG. 4 illustrates intermolecular cross-linking of collagen.

These intermolecular covalent crosslinks increase with age, (refer to FIGS. 3 and 4). As a result, the solubility of the collagen matrix in a soft tissue structure is reduced with this maturation process. Although tensile strength is increased, the collagen containing tissue becomes less compliant. Cleavage of an intermolecular bond requires approximately one ev (electron volt) of energy and can not be accomplished by heat without thermal ablation of tissue. In addition, covalent bonds are not strongly polar and will not be significantly affected by an RF current at this reduced power level. Cleavage of intermolecular covalent bonds that result in matrix remodeling without ablation is achieved by the stress created from the thermal disruption of intramolecular hydrogen bonds. Additional remodeling stress can be provided with the application of an external force that has the appropriate orientation to the fibrils of the matrix. Suitable orientations include approximately parallel to the lateral axis of the collagen fibrils. Ionic bonds are essentially intermolecular and are present in the polar regions of the fibril. Although slightly weaker than covalent bonds, thermal disruption of ionic bonds cannot occur without ablation of tissue. An RF field is an effective means to cleave these bonds and is created by the an in phase alternating ionic motion of the extracellular fluid. Frequency modulation of the RF current may allow coupling to the ionic bonds in the polar regions of the fibril. Remodeling of a target site may be optimized by the selection of a band of the spectrum that is target site specific in order to reduce collateral damage. If an optimized intrinsic absorption is insufficient then a selective medium may be provided to alter the absorption in order to discriminate various soft tissue structures. This may be achieved by altering the absorption. By altering the extracellular fluid content of a soft tissue in specific ways, the delivery of energy to a target tissue site is achieved with minimal damage to collateral structures such as skin and adjacent soft tissue structures.

The reforming of bonds at the same bond sites will diminish the remodeling process. Relaxation phenomena may inhibited with the application of an external mechanical force that separates bond sites but allows the reforming of these covalent and ionic bonds in a lengthened or contracted morphology. This can be the underlying biophysical process that occurs with the controlled remodeling of the collagen matrix. Ground substance may also function to diminish relaxation of crosslinks through competitive inhibition. Chondroitin sulfate is a highly charged molecule that is attached to a protein in a "bottle brush" configuration. This configuration promotes attachment at polar regions of the fibril and reduces the relaxation of ionic bonds in this region. As a consequence, immature soluble collagen, which has fewer intermolecular crosslinks and contains a higher concentration of ground substance, may be more easily remodeled. The induction of scar collagen through the wound healing sequence may also facilitate the remodeling process within a treatment area.

Collagen cleavage in tissue is a probability event dependant on temperature. There is a greater probability that a collagen bond will be cleaved with higher temperatures. Cleavage of collagen bonds will occur at lower temperatures but at a lower frequency. Low level thermal cleavage is frequently associated with relaxation phenomena in which there is not a net change in molecular length. An external force that mechanically cleaves the fibril may reduce the probability of relaxation phenomena. The application of an external force will also provide a means to lengthen or contract the collagen matrix at lower temperatures while reducing the potential of surface ablation. The cleavage of crosslinks with collagen remodeling may be occurring at a basal metabolic temperature that is expressed morphologically as the process of aging. Although the probability for significant cleavage in a short period of time is small, aging may be expressed as a low level steady state of collagen remodeling with the external force of gravity that becomes very significant over a period of decades. Hydrogen bonds that are relatively weak (e.g. bond strength of 0.2 to 0.4 ev) are formed within the tertiary structure of the tropocollagen molecule.

Figure 5:
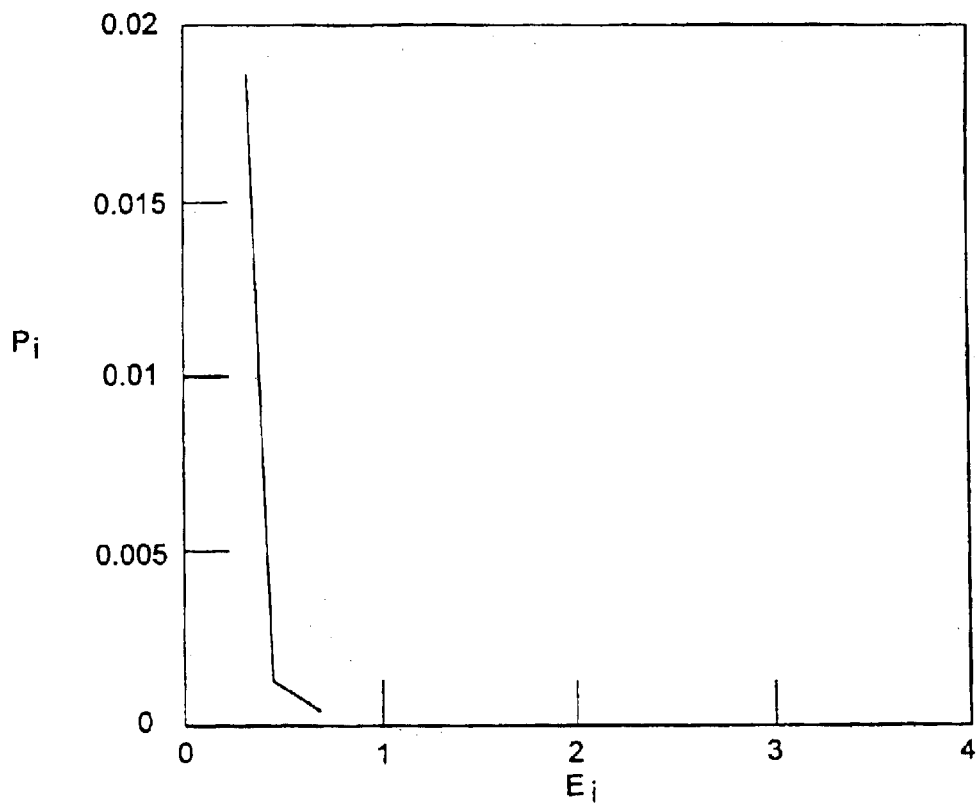
FIGS. 5 and 6 are two graphs illustrating the probability of collagen cleavage as a function of molecular bond strength at 37E C.
Figure 6:
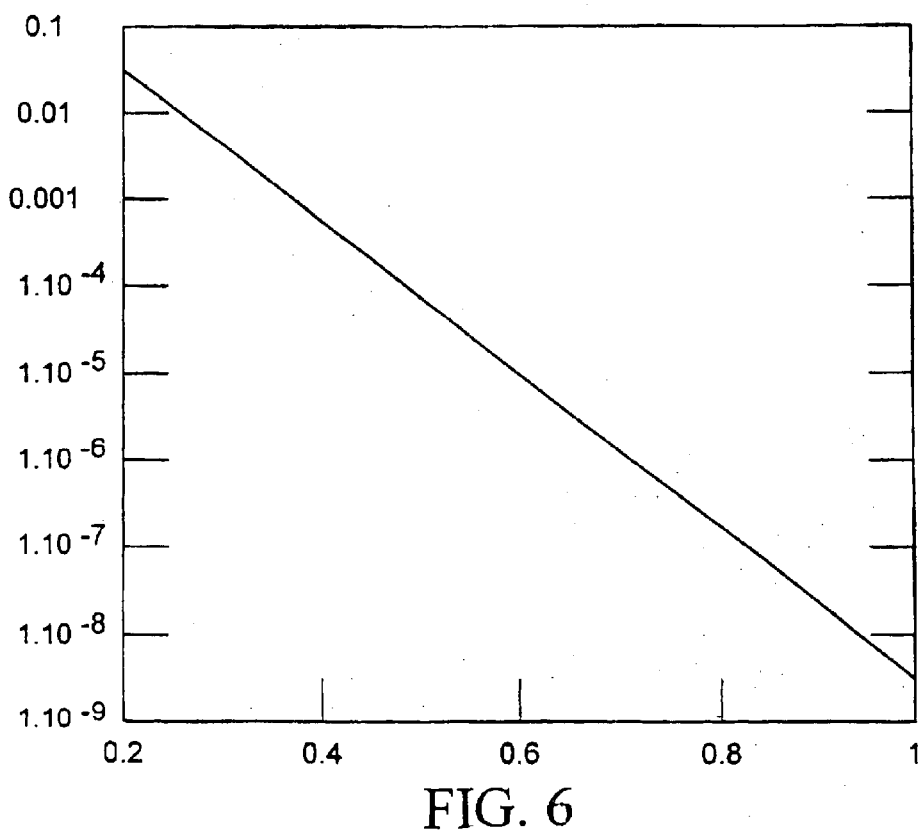

Thermal disruption of these bonds can be achieved without ablation of tissue or cell necrosis. The probability of hydrogen bond disruption at a certain temperature can be predicted by statistical thermodynamics. If a Boltzmann distribution is used to calculate the probability of bond disruption then a graph illustrating the relationship between bond strength and the probability of bond disruption at a certain temperature can be produced. Graphs of the probability of cleavage (at 37E C.) versus bond strengths are shown in FIGS. 5 and 6.

Different morphological expressions of aging may be due to the effect of gravity upon the matrix of a particular area. In areas of the skin envelope in which gravity lengthens the matrix, elastosis of skin will occur. In contrast to skin aging certain anatomical structures, such as joint ligaments, will appear to tighten with the aging process. The reduced range of motion may be due in part to the vertical vector of gravity contracting the matrix of a vertically aligned ligament. However, most of the "tightening" or reduced range of motion of joints may not be secondary to a contracted matrix but is due to reduced flexibility of the matrix caused by increased intramolecular cross-linking that occurs with aging. Essentially, the controlled remodeling of collagen is the reversal of the aging process and involves the reduction in the number of intermolecular crosslinks. As a result the remodeled matrix becomes less brittle. Greater flexibility of the soft tissue has several functional advantages including an increased range of motion of component joints.

When the rate of thermal cleavage of intramolecular crosslinks exceeds the rate of relaxation (reforming of hydrogen bonds) then the contraction of the tertiary structure of the molecule can be achieved. No external force is required for this process to occur. Essentially, the contraction of the tertiary structure of the molecule creates the initial intermolecular vector of contraction. The application of an external mechanical force during thermal cleavage will also affect the length of the collagen fibril and is determined by the overall sum of intrinsic and extrinsic vectors that is applied during a cleavage event. Collagen fibrils in a matrix exhibit a variety of spatial orientations. The matrix is lengthened if the sum of all vectors act to distract the fibril. Contraction of the matrix is facilitated if the sum of all extrinsic vectors acts to shorten the fibril. Thermal disruption of intramolecular bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming, alter lengthening or contraction of the fibril.

The amount of (intramolecular) hydrogen bond cleavage required will be determined by the combined ionic and covalent intermolecular bond strengths within the collagen fibril. Until this threshold is reached little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and non-polar regions in the lengthened or contracted fibril. The birefringence (as seen with the electron microscope) of the collagen fibril may be altered but not lost with this remodeling process. The quarter staggered configuration of the tropocollagen molecules in the native fiber exhibits a 680 D banding which either lengthens or contracts depending on the clinical application. The application of the mechanical force with template 12 during the remodeling process determines if a lengthen or contracted morphology of the collagen fibril is created. An external force of contraction will result in the contraction of the tertiary and quaternary structure of the matrix. With the application of an external distraction force, intramolecular contraction may still occur from the intrinsic vector that is inherent within its tertiary structure. However, overall lengthening of the quaternary structure of the fibril will occur due to the mechanical cleavage of the intermolecular bonds. Contraction of the tertiary structure with overall lengthening of the collagen fibril can alter the birefringence of the matrix. The altered periodicity will be exhibited in the remodeled matrix that will correlate to the amount of lengthening achieved.

Delivery of both electromagnetic energy and mechanical energy to the selected body structure involves both molecular and cellular remodeling of collagen containing tissues. The use of low level thermal treatments over several days provides an additional way to contract skin with minimal blistering and cell necrosis. Cellular contraction involves the initiation of an inflammatory/wound healing sequence that is perpetuated over several weeks with sequential and lengthy low level thermal treatments. Contraction of skin is achieved through fibroblastic multiplication and contraction with the deposition of a static supporting matrix of nascent scar collagen. This cellular contraction process is a biological threshold event initiated by the degranulation of the mast cell that releases histamine. This histamine release initiates the inflammatory wound healing sequence.

Molecular contraction of collagen is a more immediate biophysical process that occurs most efficiently with electromagnetic energy delivery devices, including but not limited to RF electrodes. The clinical setting is physician controlled and requires more precise temperature, impedance, cooling media flow and energy delivery monitoring to avoid blistering of the skin. Measured impedance will vary with the frequency of the electromagnetic energy applied to the skin surface and/or underlying soft tissue structure.

Figure 7:
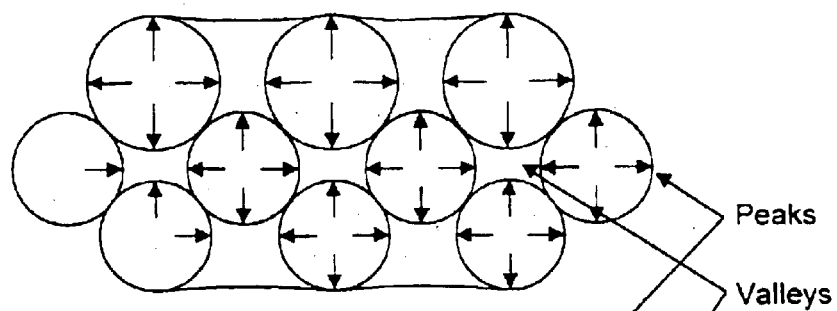
FIG. 7 is a top view of a skin surface, illustrating the peaks and valleys of the surface and the force components applied to the surface resulting from the application of a mechanical force.
Figure 8:
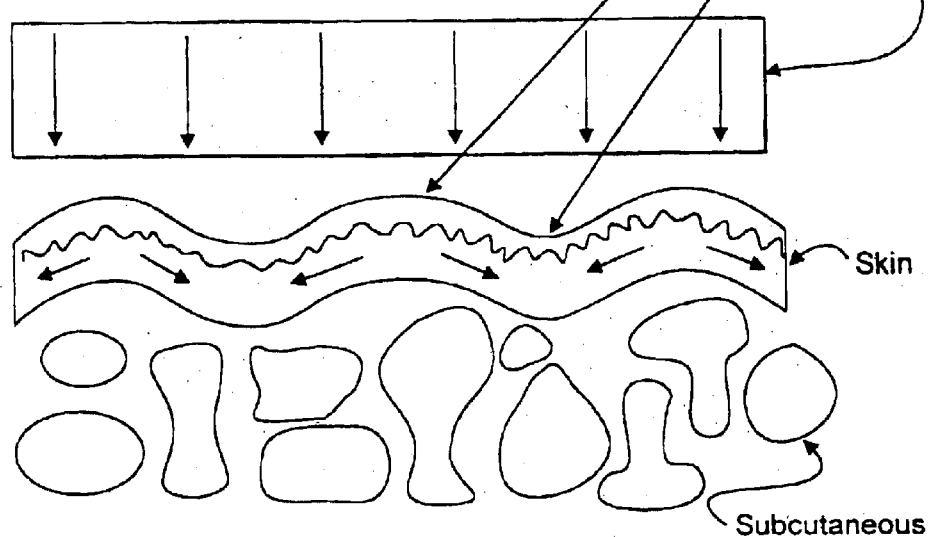
FIG. 8 is a cross-sectional view of the skin surface illustrated in FIG. 7.

Patients may be treated with one or more modalities described herein to achieve the optimal esthetic result. Refinements to the treatment area may be required using apparatus 8 in the physician's office. However, tightening of a skin surface may accentuate any preexisting contour irregularities. For this reason, conforming esthetic template 12 is used to smooth surface contour irregularities. Essentially, the application of a mechanical force upon the collagen matrix involves both contraction or distraction of the selected soft tissue structure to achieve a smoother contour. Thermal (or electromagnetic) cleavage of collagen crosslinks when combined with a mechanical force creates force vectors that contract, distract or shear the longitudinal axis of the fibril. A vector space is created with the combination of a scalar component (heat) and a force vector (an externally applied mechanical force). The force vectors within this vector space vary depending upon the specific morphology of the tissue. For example, the peaks and valleys of cellulite will have different force vectors when uniform external compression is applied. As illustrated in FIGS. 7 and 8, template 12 produces converging and diverging force vectors that act to smooth surface morphology by contracting (valleys) and distracting (peaks) the collagen matrix in a soft tissue structure. Diverging vectors on the peaks lengthen the collagen matrix while converging vectors in the valleys contract and compact the collagen matrix. The overall result is the smoothing of an irregular skin surface.

Figure 9:
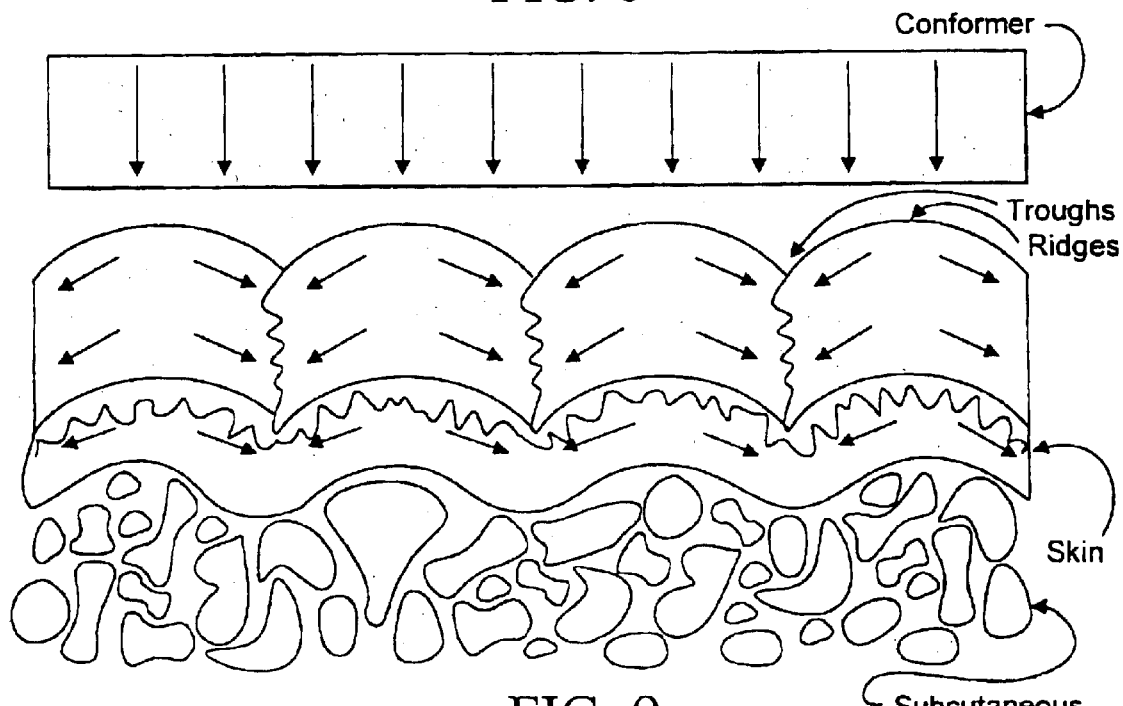
FIG. 9 is a cut-away view of the skin surface, with troughs and ridges, and underlying subcutaneous soft tissue.

Apparatus 8 may also be used to treat wrinkling of the skin. The treatment of skin wrinkles is shown in FIG. 9. In a skin wrinkle the vectors are directed perpendicular to the troughs and ridges of this contour deformity. Diverging vectors at the ridges of the skin converge in the trough of the wrinkle to smooth the surface morphology. The collagen matrix is distracted or extended at the ridges and contracted in the valleys. The overall result is the smoothing of the wrinkled skin surface.

Linear scars exhibit a similar morphology and can be remodeled with apparatus 8. Any surface irregularity with depressions and elevations will have vectors directed to the lowest point of the deformity. Prominent "pores" or acne scaring of the skin have a similar pattern to cellulite but on a smaller scale and can also be treated with apparatus 8. Clinically, the application of the mechanical force reduces the power required to remodel the matrix and diminishes cell necrosis of the skin surface as well as underlying soft tissue structures. Compression alters the extracellular fluid of the soft tissue structure (collagen) and exerts electrical impedance and thermal conductivity effects that allow delineation of a conduit-treatment interface of the collagen containing tissues. A deeper dermal interface will contract skin and exert three dimensional contour effects while a more superficial interface will smooth surface morphology.

Figure 10B:
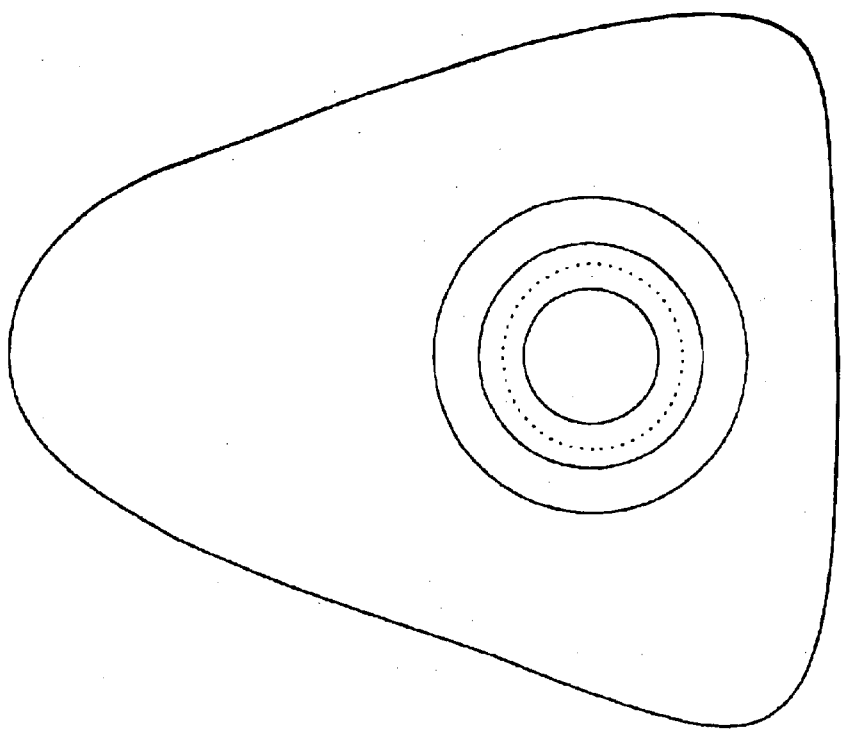
FIG. 10(b) is a front perspective view of the breast expander of FIG. 10(a).
Figure 10A:
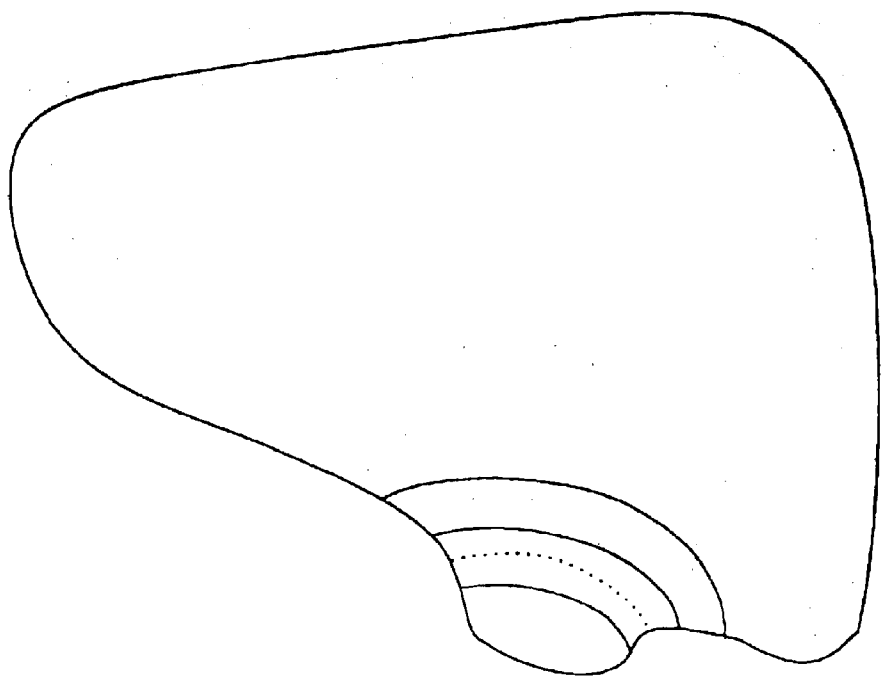
FIG. 10(a) is a lateral perspective view of a telescoping segment of a breast expander useful with the apparatus of FIG. 1.
Figure 10C:
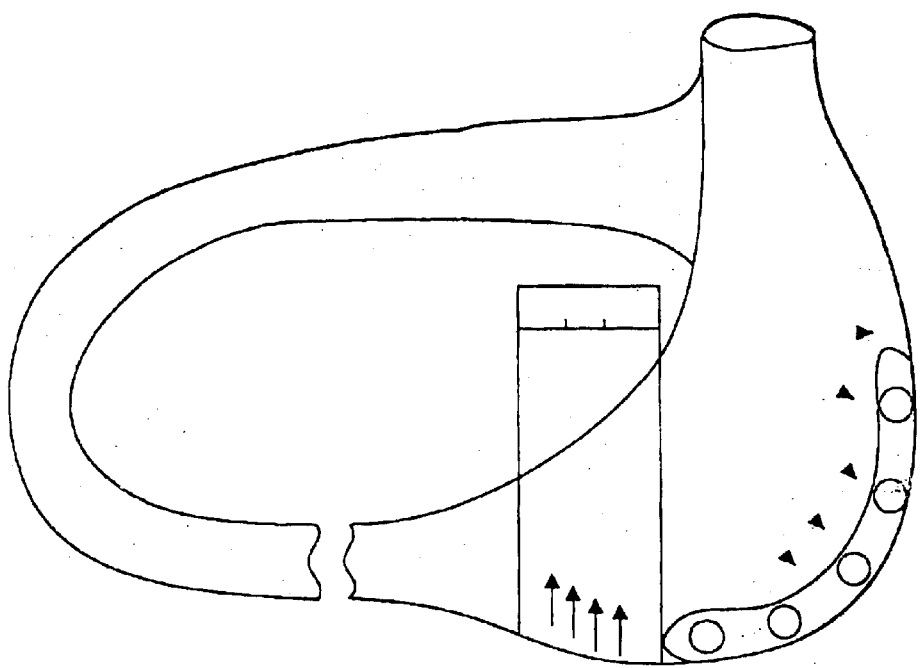
FIG. 10(c) illustrates a bra which functions as the template of FIG. 1.
Figure 10E:
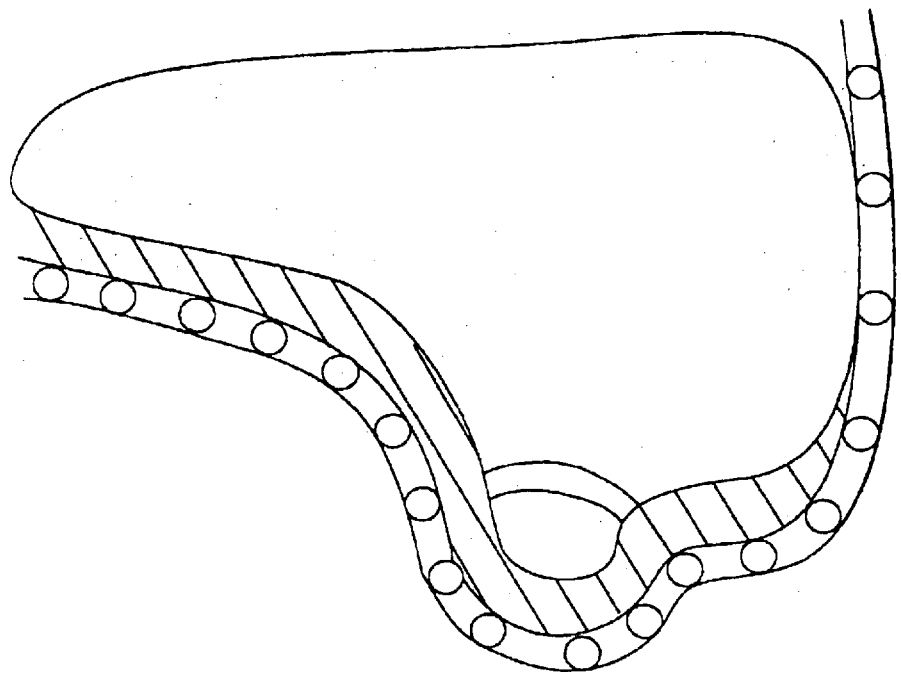
FIG. 10(e) is a lateral cross-sectional perspective view of a fully expanded breast expander within a breast.
Figure 10D:
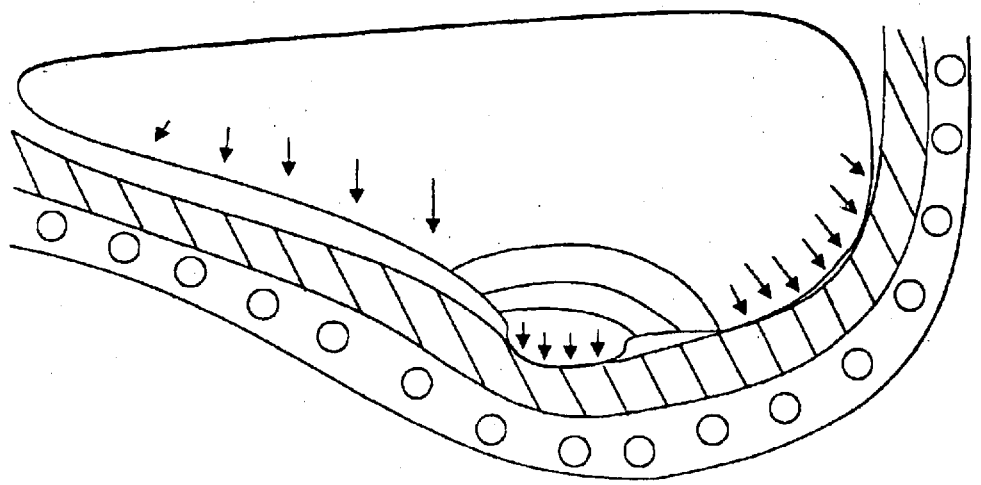
FIG. 10(d) is a lateral cross-sectional perspective view of a partially expanded breast expander within a breast.

In circumstances in which expansion of the skin envelope is needed, the combined application of heat and pressure is also required. For breast reconstruction, expansion of the skin envelope is typically achieved with each inflation of a subpectoral breast expander. FIGS. 10(a) and 10(b) illustrate an expander with an RF receiver electrode. A telescoping segment with an RF energy source is incorporated with access valve and is used to expand a nipple areolar donor site for Pectoralis "Peg" Procedure. The segmental expander can also be used to prepare the recipient site for delayed autologous "Peg" Flap. The pressure that is exerted on the skin and the periprosthetic scar capsule is from the inside. In this application, vectors are directed outward. As an adjunct to this expansion process, a controlled thermal pad may be incorporated into a bra, as illustrated in FIG. 10(c), which can be applied to the inferior pole of the breast skin to promote lengthening of collagen fibril within the skin and underlying scar capsule around the expander. The bra may also function as an external conforming template 12 to achieve a specific breast shape. The net result is the creation of a more esthetic breast reconstruction with three dimensional characteristics of the opposite breast. In a like manner, other garments can be utilized as external conforming templates for other anatomical body structures. In FIG. 10(d) a breast expander is partially expanded within the breast. In FIG. 10(e), the expander is fully expanded within the breast.

Template 12 applies a mechanical force in combination with the delivery of energy to the skin surface and underlying soft tissue structure, to remodel collagen both esthetically and functionally with minimal thermal damage including cell necrosis. Additionally, template 12 can be configured (as described herein) to deliver both mechanical force and energy while minimizing or reducing edge effects. These effects comprise both electrical and pressure edge effects describe herein.

Figure 11:
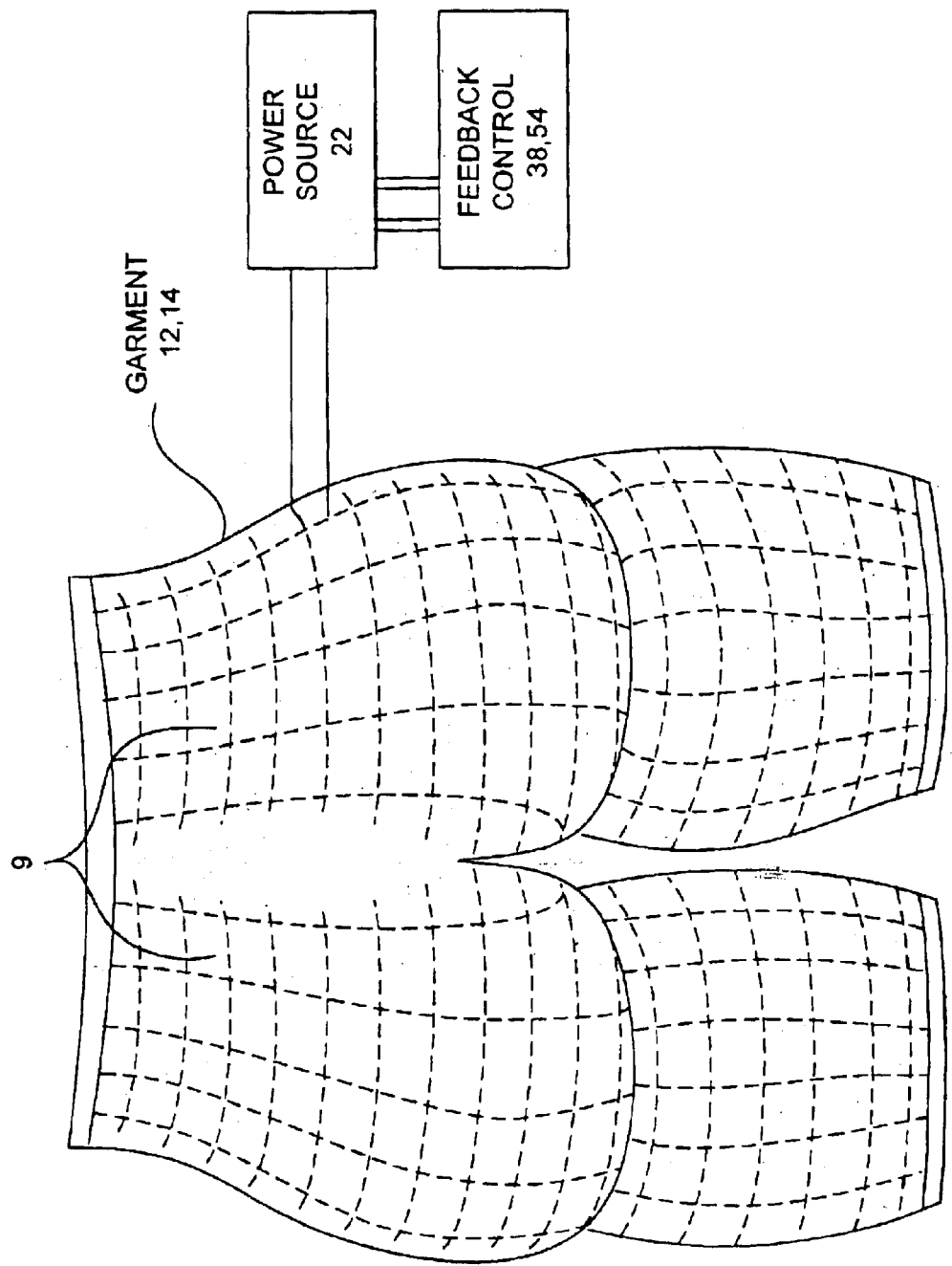
FIG. 11 illustrates a template in the form of a garment.

In various embodiments, template 12 can be configured to treat a variety of human anatomical structures (both internal and external) and accordingly, can have a variety of different forms, including but not limited to, a garment that is illustrated in FIG. 11. An energy source 22 can be directly incorporated into the fabric of a tight fitting garment or inserted as a heating or RF electrode pad into a pocket of the garment. Another example of a garment is a tight fitting bra that extends over the arm and waistline with zone control that provides contraction of the skin of the breast, arms, and waistline to a variable amount to create a desired three-dimensional figure. Functional remodeling of collagen containing structures include a variety of different applications for aesthetic remodeling.

Figure 12A:
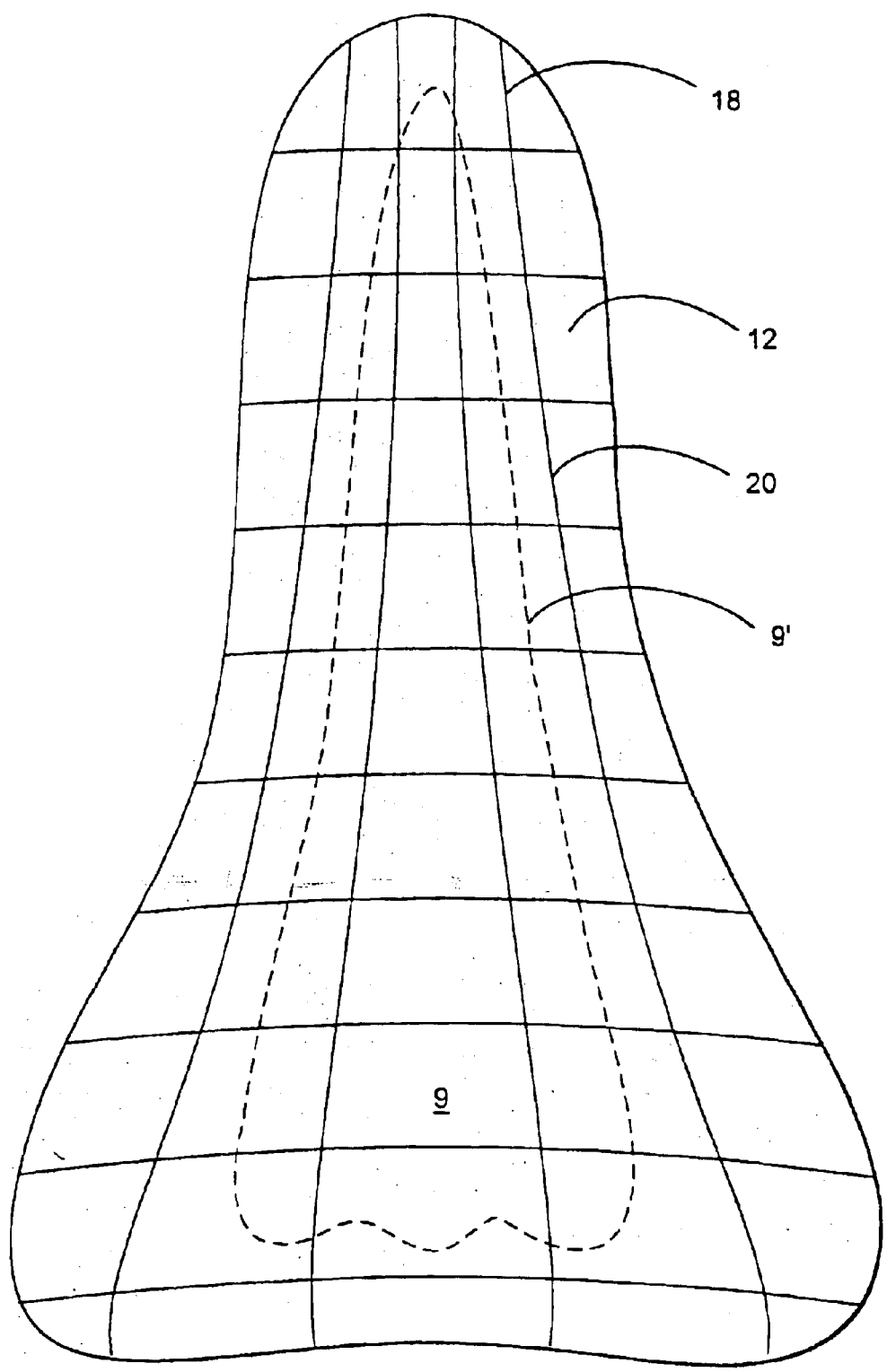
FIG. 12(a) illustrates a template that is positioned over a nose.
Figure 12B:
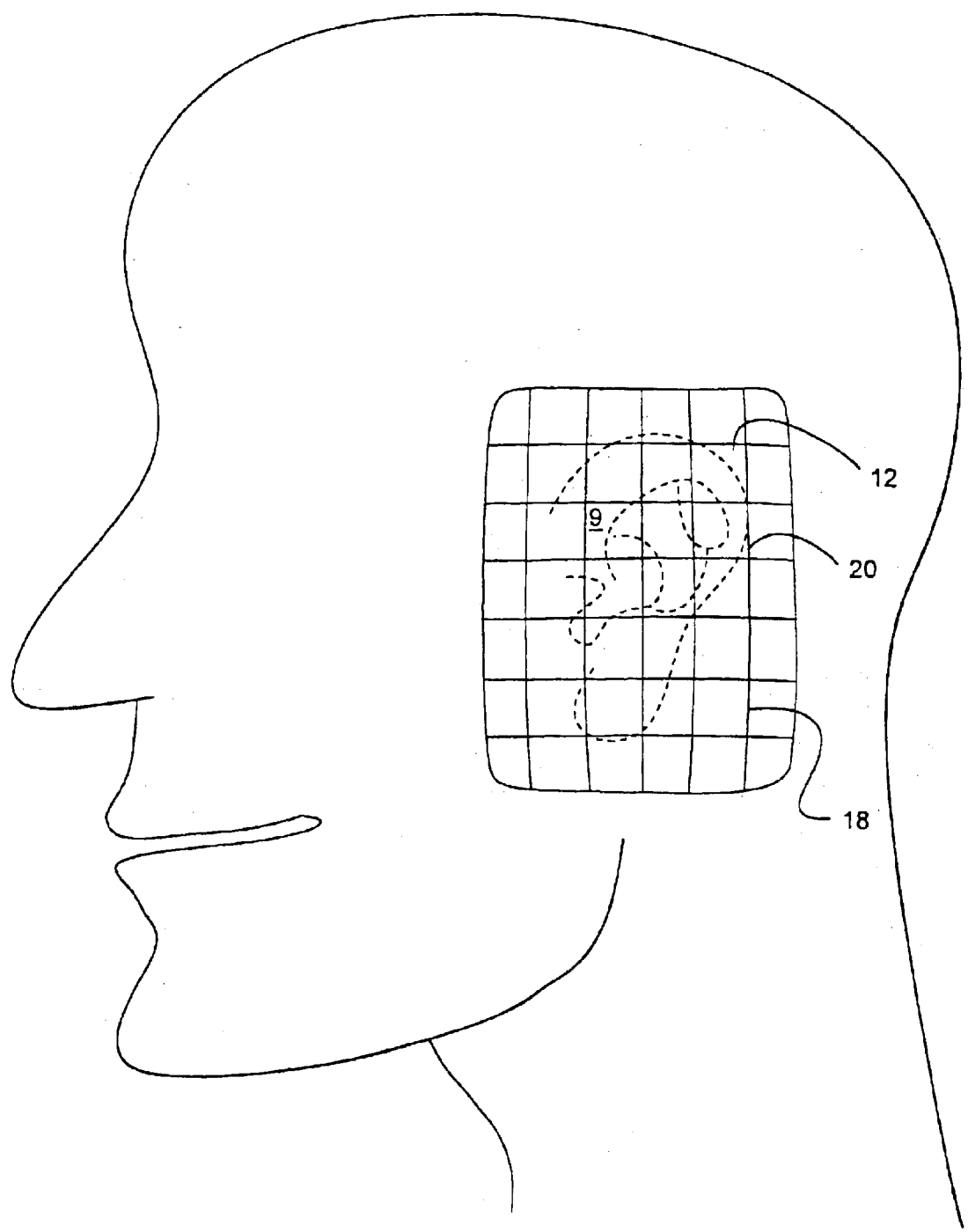
FIG. 12(b) illustrates a template that is positioned over an ear.

As shown in FIGS. 12(a) and 12(b), in various embodiments template 12 can be a garment positioned over the nose, around the ear, or other facial structure.

Figure 13:
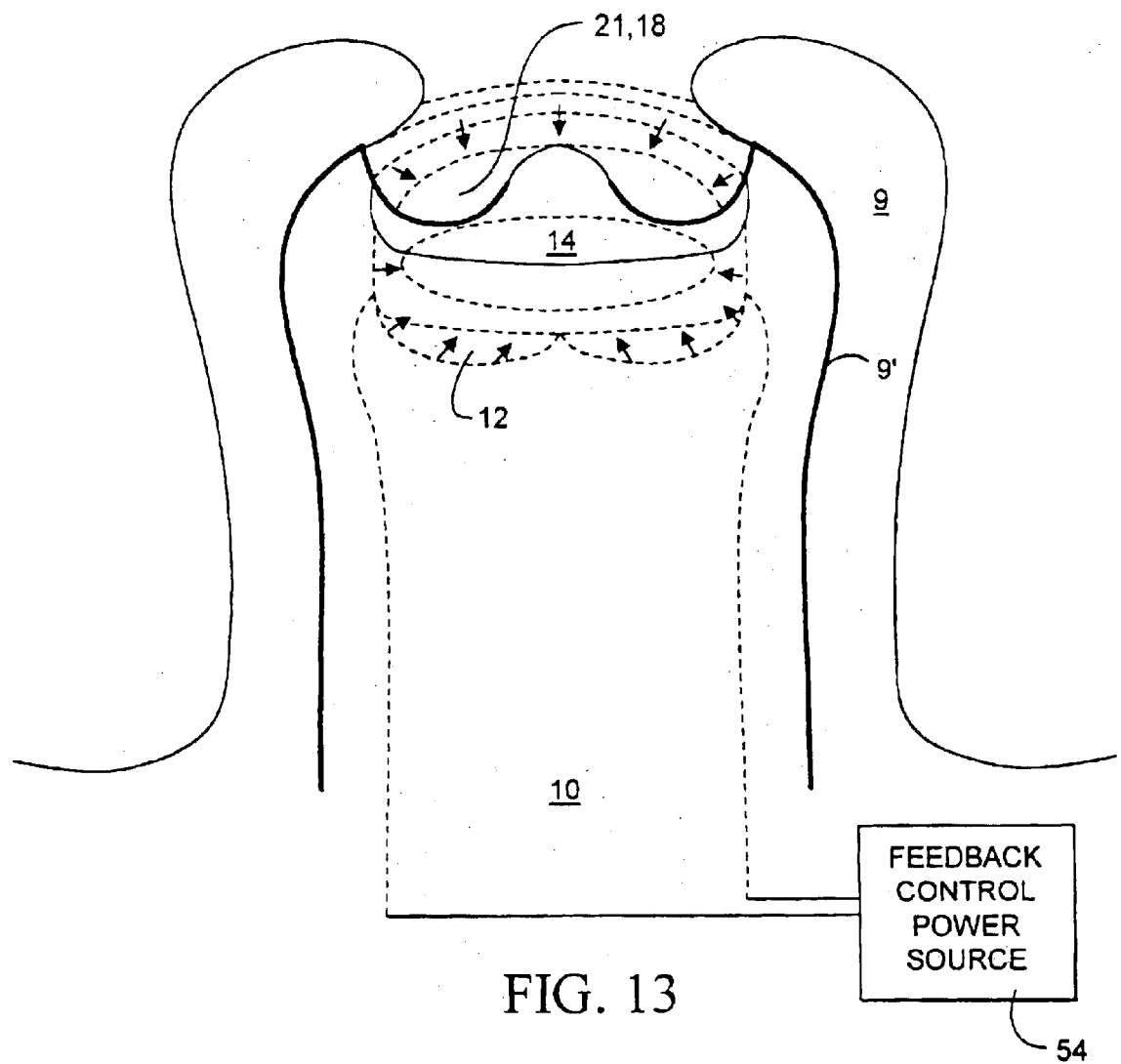
FIG. 13 is a perspective view of a template that is useful in the cervix.
Figure 14:
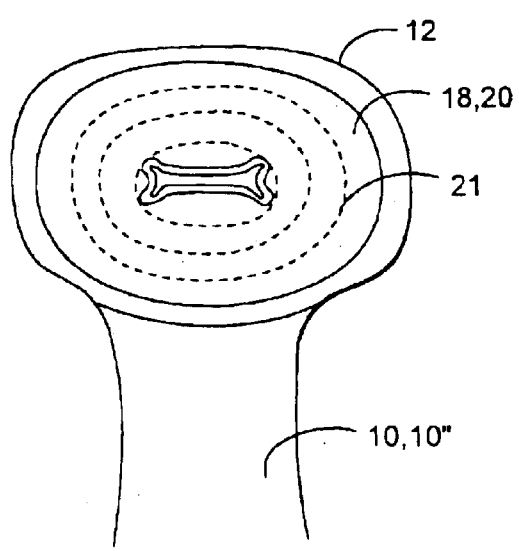
FIG. 14 is a cross-sectional view of the template of FIG. 13.

Template 12 can also be applied for functional purposes. Referring now to FIGS. 13 and 14, pre-term cervical dilation can be treated with a template 12 that is the impression "competent" cervix. The cervical template 12 create vectors that contract the circumference of the cervix. The incorporated energy delivery device 18 contracts the native matrix and induces scar collagen. The dilated cervical OS is tightened and the entire cervix is strengthened. Energy delivery device 18 can be incorporated into template 12 which can be the cervical conformer and inserted as a vaginal obturator. It will be appreciated that template 12 can be utilized for other functional treatments.

Figure 15A:
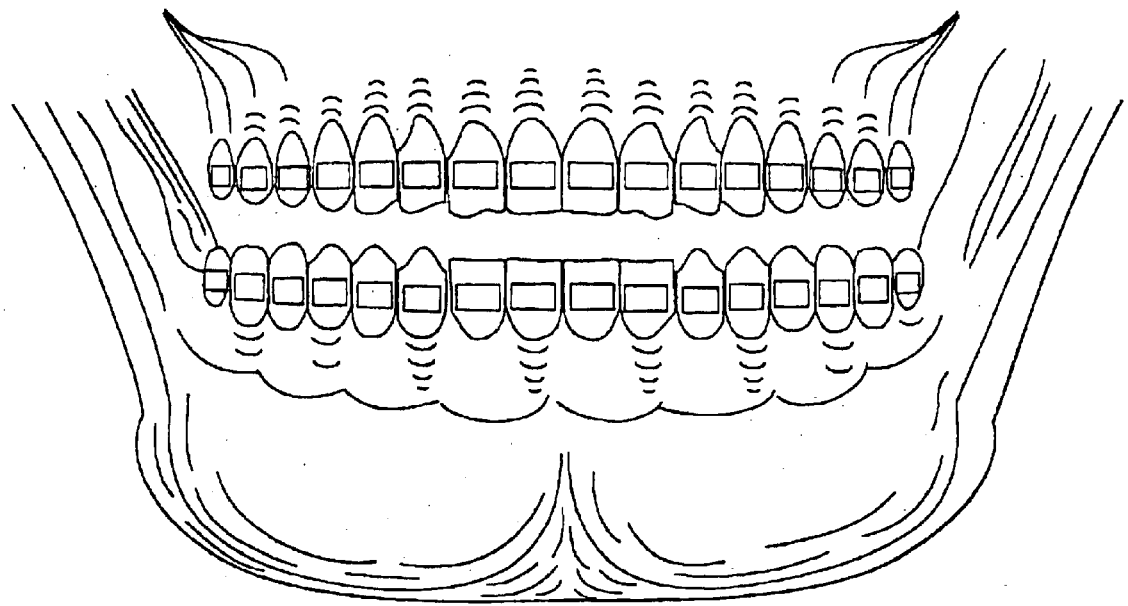
FIG. 15(a) is a front view of an orthodontic appliance that includes RF electrodes.
Figure 15B:
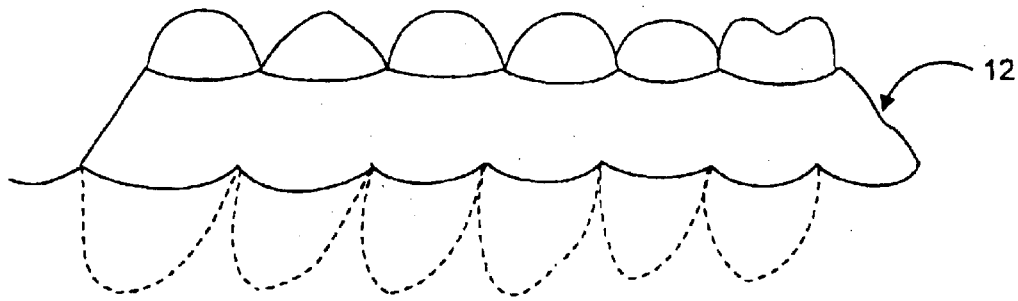
FIG. 15(b) is perspective view of an orthodontic appliance template of the device of FIG. 1.
Figure 15C:
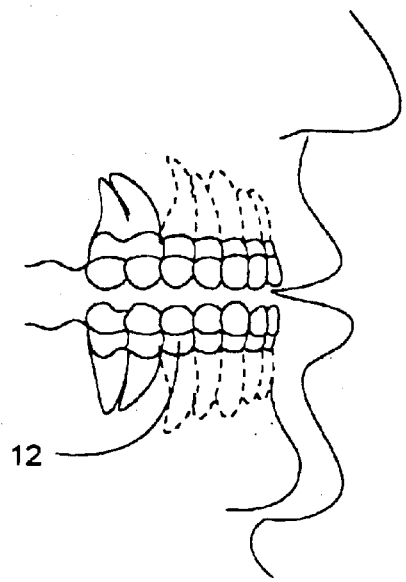
FIG. 15(c) is cross-sectional view of the template of FIG. 15(b)

In another embodiment, template 12 is a functional appliance that may be nonconforming and can be separate or incorporated with the energy delivery device 18. Orthodontic braces that are designed in conjunction with energy delivery device 18 are used to remodel dental collagen and apply rotation and inclination vectors on the neck of the tooth which is devoid of enamel. In FIG. 15(a) orthodontic braces are coupled to RF electrodes and associated power source. The orthodontic braces function as a nonconforming force application surface that is coupled to incorporated RF electrodes. FIGS. 15(b) and 15(c) illustrates a orthodontic appliance that is a conforming template 12 coupled to RF electrodes. As a consequence, orthodontic correction is more rapidly achieved than current modalities that employ only mechanical forces. Orthodontic correction can also be achieved with a conforming template 12 that is the corrected impression of the patient's dentition.

For orthopedic applications, an external fixation device is used as a nonconforming functional appliance. This appliance is used in tandem with an energy source device, including but not limited to RF electrodes, that remodels the collagen of the callus tissue. More accurate alignment of osteotomy and fracture sites are possible with either a conforming or nonconforming brace that is used in tandem or is directly incorporated into energy delivery device 18. Improved range of motion of contracted joints and correction of postural (spinal) deformities can be achieved with this combined approach.

The ability to remodel soft tissue in anatomical structures other than skin is dependent upon the presence of preexisting native collagen. In tissue devoid or deficient of native collagen, energy and/or force can be delivered to cause an induction or formation of scar collagen. Template 12 can be used to remodel the subcutaneous fat of hips and thighs in addition to the tightening of the skin envelope. The convolutions of the ear cartilage can be altered to correct a congenital prominence. The nasal tip can be conformed to a more esthetically pleasing contour without surgery.

Template 12 can be used with any modality that remodels collagen including but not limited to the applications of heat, electromagnetic energy, force and chemical treatment, singularly or in combination. In addition to RF (e.g. molecular) remodeling of collagen, cellular modalities that invoke the wound healing sequence can be combined with a conforming esthetic template. Thermal and chemical treatments (e.g. glycolic acid) induce a low-level inflammatory reaction of the skin. Scar collagen induction and fibroblastic (cellular) contraction are directed into converging and diverging vectors by a conformer that produces a smoother and tighter skin envelope. In addition to achieving a smoother and tighter integument, the texture of the skin is also improved with this remodeling process. Older or less compliant skin has a greater number of intermolecular crosslinks in the dermal collagen than younger skin. Scar collagen induction with cleavage of crosslinks will produce a softer and more compliant skin envelope.

Cutaneous applications for apparatus 8 include the following: (i) Non invasive skin rejuvenation with the replacement of elastoic sun damaged collagen in the dermis with nascent scar collagen, (ii) on invasive hair removal, without epidermal burning, (iii) Hair growth with intracellular induction of the hair follicle, (iv) Non invasive reduction of sweating and body odor, (v) Non invasive reduction of sebaceous gland production of oil as a treatment of an excessively oily complexion, and (vi) Non invasive treatment of dilated dermal capillaries (spider veins). Noncutaneous applications for apparatus 8 include the following: (i) Non invasive treatment of preterm delivery due to an incompetent cervix, (ii) Non invasive treatment of pelvic prolapse and stress incontinence, (iii) Non invasive treatment of anal incontinence, (iv) Non invasive creation of a continent ileostomy or colostomy, and (v) Non invasive (or minimally invasive through an endoscope) correction of a hernia or diastasis.

Figure 16:
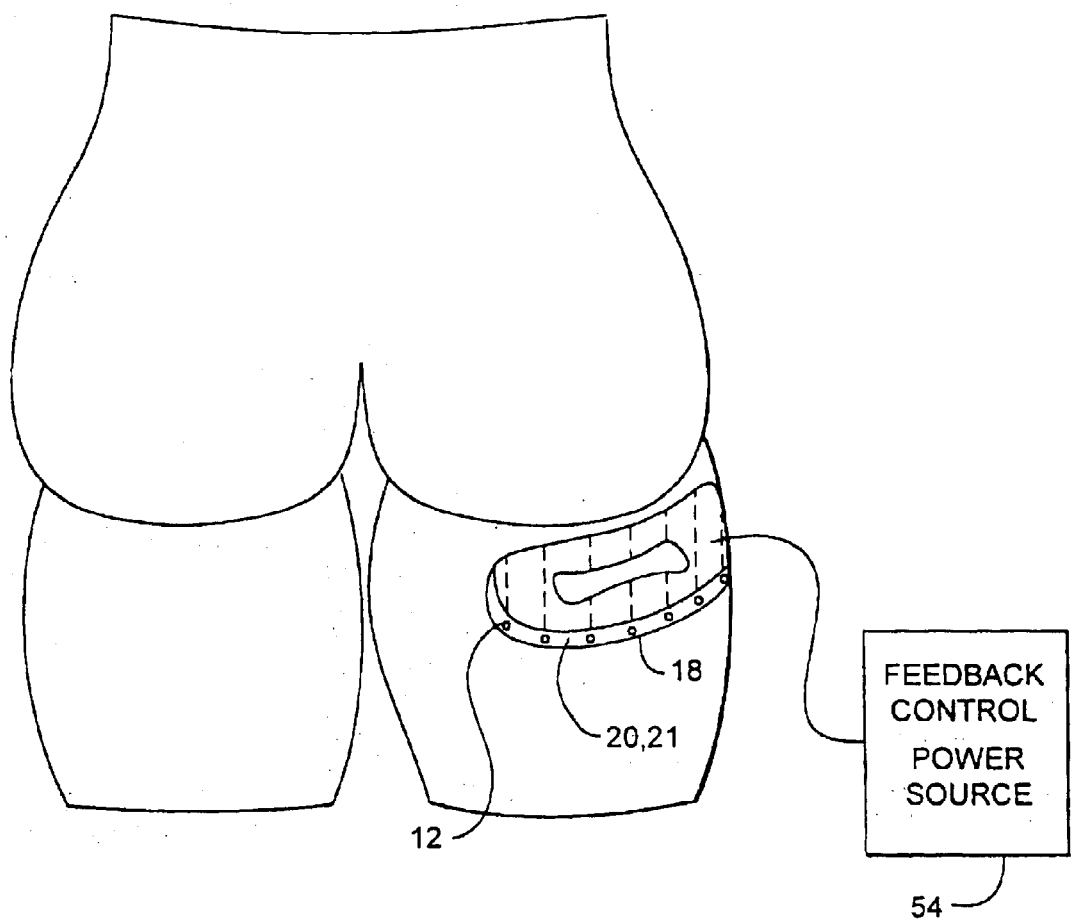
FIG. 16 is a perspective view illustrating a template made of a semisolid material that becomes more conforming to underlying soft tissue upon the application of a mechanical force.
Figure 17:
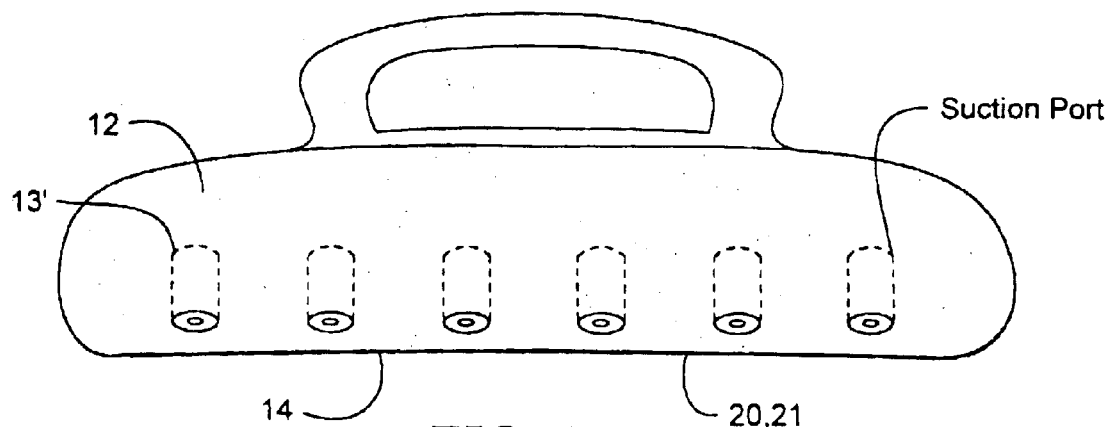
FIG. 17 illustrates a template with an adherent or suction mechanical force delivery surface that permits manual manipulation of skin and soft tissue structures.

Referring now to FIGS. 16 and 17, template 12 can be stationary or mobile. A hand held conforming template 12 that is mobile provides the practitioner with greater flexibility to remodel the collagen matrix and surrounding tissue. Pressure (e.g. force) and impedance changes can serve as a guide for the manual application of template 12. A hand held template 12 with an incorporated energy source 22 and energy delivery devices 18 may be applied over a conductive garment that provides three dimensional conformance to the treatment area. Less accessible areas can be remodeled with this particular device. In one embodiment shown in FIG. 16, template 12 is made of a semisolid material that conforms a lax skin envelope to an underlying soft tissue structure. The semi-solid material allows for the customized shaping of force application surface 14 and reduces the need for precise fabrication of an esthetic template. Suitable semi-solid materials include compliant plastics that are thermally and electrically conductive. Such plastics include but are not limited to silicone, polyurethane and polytetrafluorothylene coated or otherwise embedded with an electrically or thermally conductive metal such as copper, silver, silver chloride, gold, platinum or other conductive metal known in the art.

Controlled remodeling of collagen containing tissue requires an electromagnetic device that lengthens or contracts the matrix with a minimum of cell necrosis. Energy delivery devices suited to this purpose include one or more RF electrodes. Accordingly, energy delivery device 18 can include a plurality of RF electrodes with or without insulation. The non-insulated sections of the RF electrodes collectively form template energy delivery surface 20. In a similar manner in various other embodiments, microwave antennas, optical waveguides, ultrasound transducers and energy delivery or energy remove fluids can be used to form template energy delivery surface 20. Individual electrodes 18 and the like can be multiplexed and to provide selectable delivery of energy.

Figure 18A:
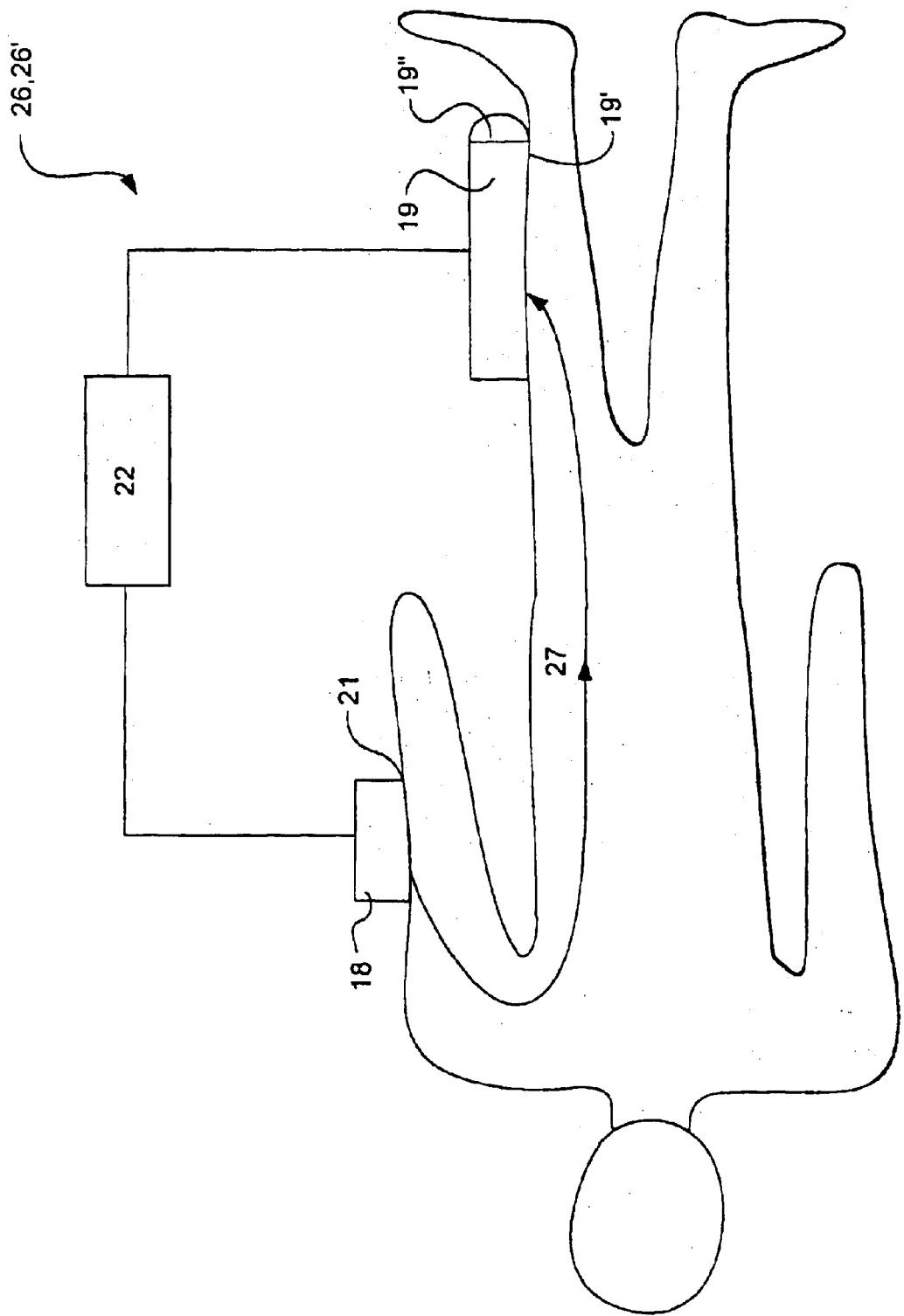
FIG. 18a is a schematic diagram illustrating a monopolar RF energy system including the use of a ground pad electrode.
Figure 18B:
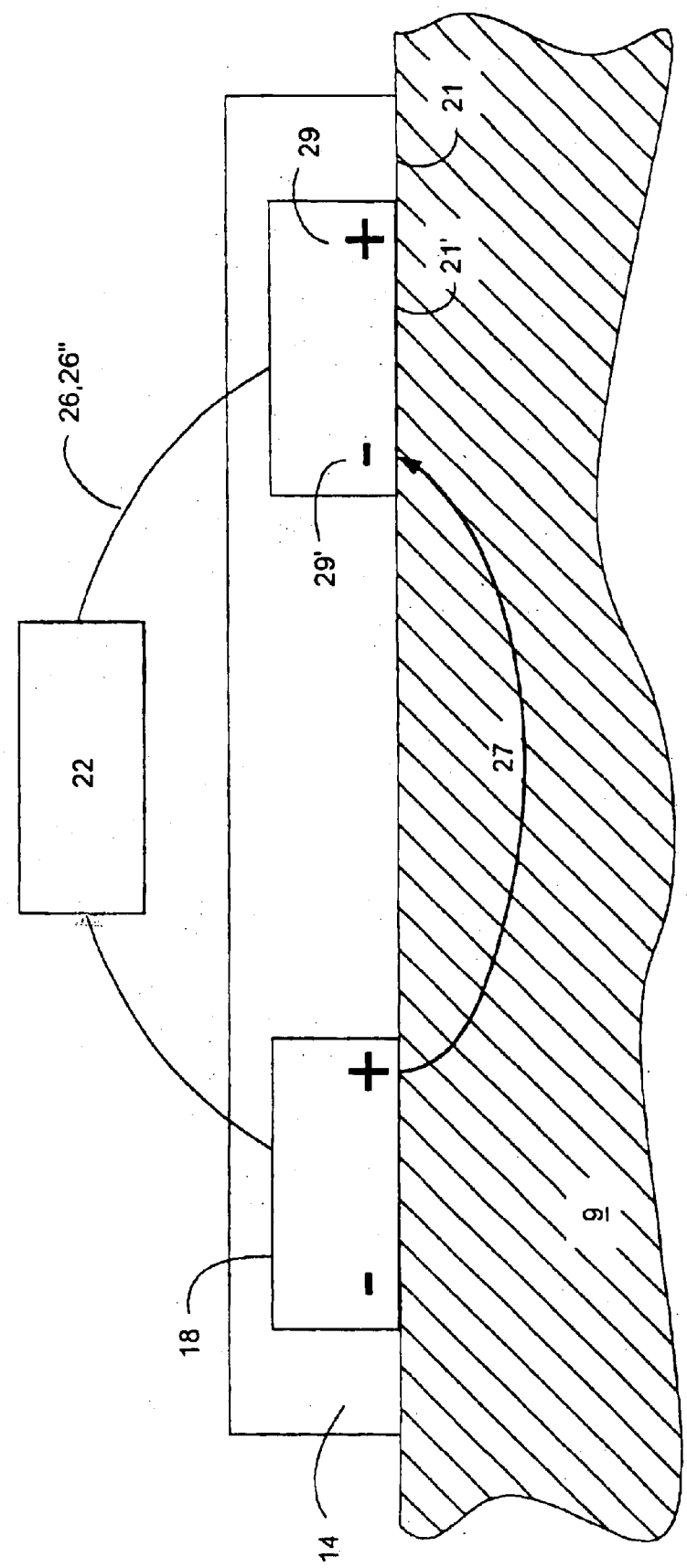
FIG. 18b is a schematic diagram illustrating a bipolar RF energy system and bipolar RF energy electrode.

Referring now to FIGS. 18a and 18b, when energy delivery device 18 is an RF electrode, energy source 22 is a RF generator well known in the art, together they comprise an RF energy delivery system 26. RF energy system 26 can be operated in either a bipolar or a monopolar configuration as is well known in the art of electrosurgery. A monopolar RF energy system 26' tends to behave as a series circuit if tissue surface impedance is uniform. In various monopolar embodiments, tissue surface impedance can both be reduced and made more uniform by hydration of the skin surface and/or underlying tissue. This in turn should reduce resistive heating of the skin surface. Such a monopolar system configuration will be less likely to produce high current density shorts than a bipolar system. The resulting electrical field will also have greater depth if heating of subjacent tissues is desired. It is predicted that the application of uniform compressive forces to the skin with monopolar RF systems can be used to actively remodel the dermis instead of being a factor that causes a combined edge effect at the skin surface. In addition, a monopolar system 26' provides a choice of two treatment surfaces. Another embodiment of a monopolar system 26' involves the combination of RF lipolysis at the active electrode with skin contraction at the passive electrode tissue interface 19' and surrounding tissué.

As shown in FIG. 18a, in a monopolar RF energy system 26' current flows from RF energy source 22 to the RF electrode 18 also known as the active electrode 18, into the patient and then returns back to RF generator 22 via a second electrode 19 known as a passive electrode 19, return electrode 19, or ground pad 19 which is in electrical contact with the skin of the patient (e.g the thigh or back). In various embodiments, RF electrode 18 can be constructed from a variety of materials including but not limited to stainless steel, silver, gold, platinum or other conductor known in the art. Combinations or alloys of the aforementioned materials may also be used.

Ground pad 19 serves to both provide a return path for electrical current 27 from electrode 18 to electrical ground and disperse the current density at ground pad tissue interface 19' to a sufficiently low level so as to prevent a significant temperature rise and or thermal injury at interface 19'. Ground pad 19 can be either a pad or a plate as is well known in the art. Plates are usually rigid and made of metal or foil-covered cardboard requiring use of a conductive gel; pads are usually flexible. Suitable geometries for ground pad 19 include circular, oval or rectangular (with curved corners) shapes. Heating at tissue interface 19 can be reduced in various embodiments in which ground pad 19 has a radial taper 19". Ground pad 19 may also contain a heat transfer fluid or be coated with a thermally conductive material to facilitate even distributions of heat over the pad, reduce hot spots and reduce the likelihood of thermal injury at tissue interface 19'. Also ground pad 19 and the interface 19' between ground pad 19 and the patient is of sufficiently low impedance to prevent the phenomena of current division, or electrical current flowing to ground by an alternate path of least resistance and potentially burning of the patients skin at an alternate grounded site on the patient. Furthermore, ground pad 19 is of sufficient surface area with respect to both the patient and with RF electrode 18 such that the return current is dispersed to a level that the current density at interface 19' is significantly below a level that would cause damage or any appreciable heating of tissue at interface 19' or any other part of the body except in the area 21 in immediate proximity to RF electrode 18. In various embodiments, the surface area of ground pad 19 can range from 0.25 to 5 square feet, with specific embodiments of 1, 2, 3 and 4 square feet.

In alternative embodiments, grounding pad 19 is used as the surface treatment electrode. That is, it functions to produce a heating effect at tissue interface 19' in contact with ground pad 19. In these embodiments, the surface area of ground pad 19 is small enough relative to both the patient and/or RF electrode 18 such that ground pad 19 acts as the active electrode. Also, RF electrode 18 has a large enough surface area/volume (relative to the patient) not to produce a heating effect at energy delivery surface 20. Also, ground pad 19 is positioned at the desired treatment site, while RF electrode 18 is electrically coupled to the patients skin 9' a sufficient distance away from return electrode 19 to allow sufficient dispersion of RF current 27 flowing through the patient to decrease the current density and prevent any heating effect beside that occurring at pad interface 19'. In this embodiment, fluid delivery device 13 can be incorporated into the ground pad 19. The subjacent skin is hydrated to reduce resistive heating and provide a more uniform impedance that will avoid parallel shorts through localized areas of low impedance. At a distant tissue site, active electrode 18 is applied either topically cooled or inserted percutaneously with a sheathed electrode that avoids burning of the skin. The active electrode 18, will be typically positioned in the subcutaneous fat layer. The fat is injected with a saline solution to lower current density which will in turn diminish burning of the subcutaneous tissue. If significant burning of the subcutaneous tissue occurs, this site can be positioned on the lower abdomen for an aesthetic excision.

Referring now to FIG. 18b, in a bipolar RF energy system 26", individual RF electrodes 18 have positive and negative poles 29 and 29'. Current flows from the positive pole 29 of one electrode to its negative pole 29', or in a multiple electrode embodiment, from the positive pole 29 of one electrode to the negative pole 29' of an adjacent electrode. Also in a bipolar embodiment, the surface of a soft or conformable electrode 18 is covered by a semiconductive material describe herein. Also in a bipolar system it is important that the force applied by force applications surface 14 to tissue interface 21 be limited to that amount necessary only to achieve and maintain contact with the skin. This can be achieved through the use of a feedback control system described herein.

In various embodiments, RF electrode 18 can be configured to minimize electromagnetic edge effects which cause high concentrations of current density on the edges of the electrode. By increasing current density, edge effects cause hot spots in tissue interface 21 or on the edges of the electrode resulting in thermal damage to the skin and underlying tissue at or near tissue interface 21.

Referring now to FIGS. 19a and 19b, the reduction of edge effects can be accomplished by optimizing the geometry, design and construction of RF electrode 18. Electrode geometries suited for reducing edge effects and hot spots in RF electrode 18 and tissue interface 21 include substantially circular and oval discs with a radiused edge 18". For the cylindrical configuration edge effects are minimized by maximizing the aspect ratios of the electrode (e.g. diameter/thickness). In a specific embodiment, edge effects can be also reduced through the use of a radial taper 43 in a circular or oval shaped electrode 18. In related embodiments, the edges 18" of electrode 18 are sufficiently curved (e.g. have a sufficient radius of curvature) or otherwise lacking in sharp corners so as to minimize electrical edge effects.

Figure 20A:
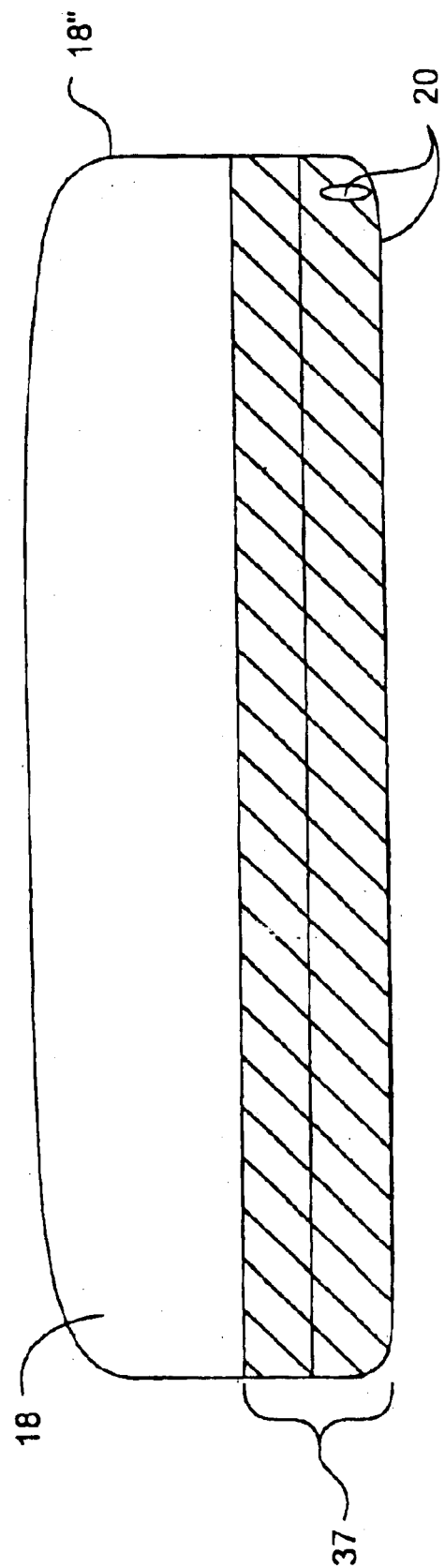
FIG. 20a is a lateral view illustrating the use of conforming layers with an RF electrode configured to reduce edge effects.
Figure 20B:
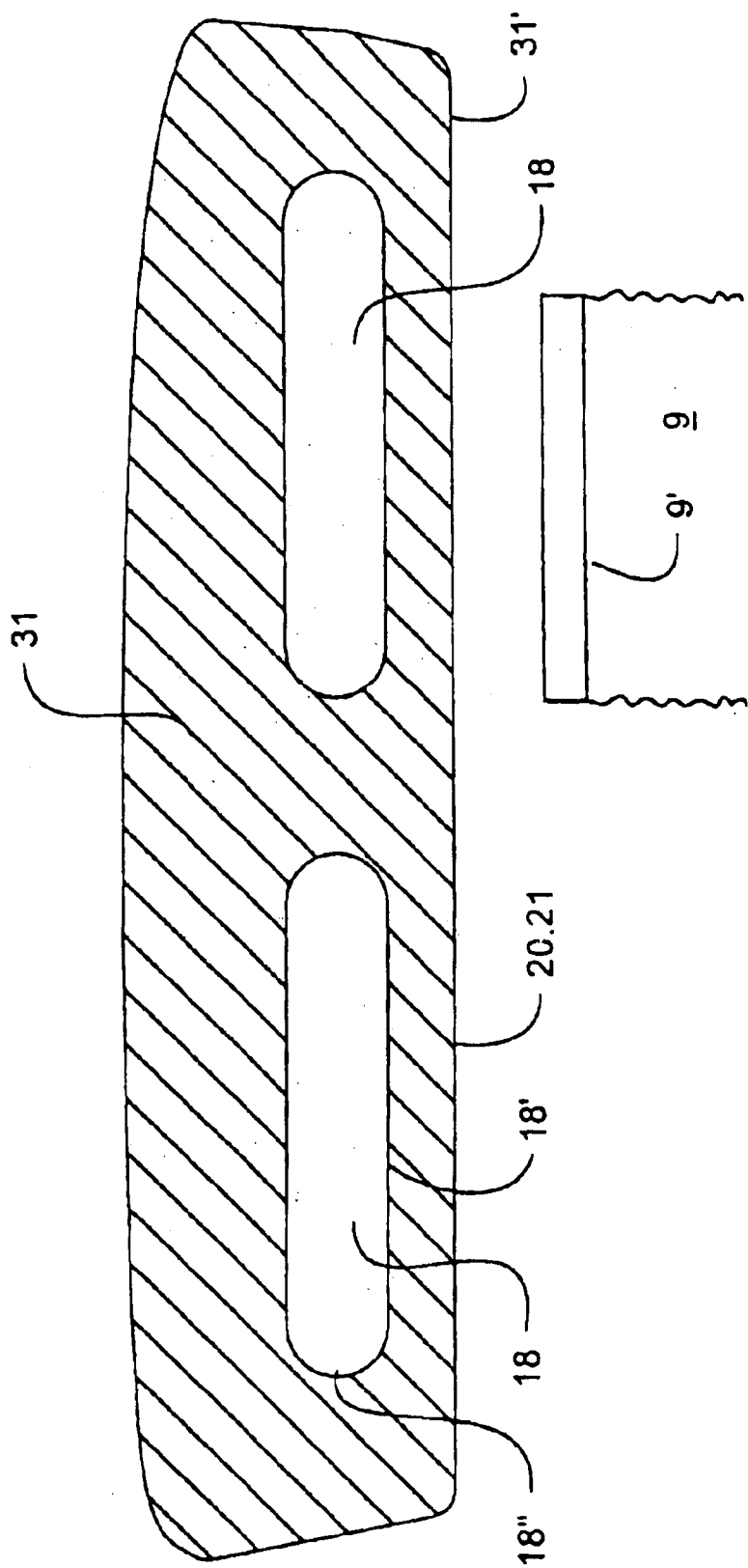
FIG. 20b is a lateral view illustrating the use of semiconductive material template with an RF electrode configured to reduce edge effects.

Referring now to FIGS. 20a and 20b, the are several other embodiments of RF electrode 18 that can reduce edge effects. One embodiment illustrated in FIG. 20a, involves the use of a soft or conforming electrode 18 that has a soft or conforming layer 37 over all or a portion of its energy delivery surface 20. Conforming layer 37 can be fabricated from compliant polymers that are embedded or coated with one or more conducting materials (in the case of monopolar embodiments described herein) including, but not limited to silver, silver chloride, gold or platinum.

In bipolar embodiments, conforming layer 37 is coated or otherwise fabricated from semiconductive materials described herein. The polymers used are engineered to be sufficiently compliant and flexible to conform to the surface of the skin while not protruding into the skin, particularly along an edge of the electrode. The conducive coatings can be applied using electrodeposition or dip coating techniques well known in the art. Suitable polymers include elastomers such as silicone and polyurethanes (in membrane or foam form) and polytetrafluoroethylene. In one embodiment the conformable template surface 37 will overlap the perimeter 18" of electrode 18 and cover any internal supporting structure. In another embodiment the entire surface 20 of electrode 18 is covered by conforming layer 37.

Referring now to FIG. 20b, in various embodiments, particularly those using an array of RF electrodes 18, edge effects at the electrode tissue interface 21 can be reduced by the use of a semiconductive material template 31 or substrate 31 located between or otherwise surrounding electrodes 18. In various embodiments, the conductivity (or impedance) of semiconductive substrate 31 can range from $10^{-4}$ to $10^{3}$(ohm-cm)$^{-1}$, with specific embodiments of $10^{-4}$ and 1 (ohm-cm)$^{-1}$. The conductivity (or impedance) of substrate 31 can also vary in a radial 31' or longitudinal direction 31" resulting in an impedance gradient.

In various embodiments, surrounding means that substrate 31 is in contact with and/or provides an electrical impedance at all or a portion of electrode 18, including but not limited to, only one or more surfaces 18', and one or more edges 18". In this and related embodiments substrate 31 is an insulating material with a conductivity of $10^{-6}$ (ohm-cm)$^{-1}$ or lower.

The impedance of the semiconductive template 31 can be variable in relation to electrode position within template. The template impedance has a specific pattern that reduces hot spots on the tissue surface 9' by reducing current density at locations more likely to have higher current densities such as edges of individual electrodes and the array itself. In one embodiment, the impedance of template 31 is larger at the electrode perimeter or edges 18". Also in various embodiments, electrode shape and topographical geometry are incorporated into the variable impedance topography of semiconductive template 31 between the electrodes. As a result, a more uniform current density is achieved that prevents or reduces thermal damage of tissue at or nearby tissue interface 21. The specific electrode shape, geometry and distribution pattern on the variable impedance template 31 as well as the pattern of impedance variation over the template surface 31' can be modeled and designed using a software simulation (such as a finite element analysis program) that is adapted for the overall three-dimensional contour of a specific device.

In addition to electromagnetic edge effects described herein, pressure edge affects may also result with the use of a rigid materials in force application surface 14 that tend to concentrate force on the edges of force application surface 14 and/or electrode 18. Such force concentrations can damage skin and underlying tissue and also cause hot spots due to increased RF energy delivery and/or increased heat transfer at the areas of force concentration.

Figure 21:
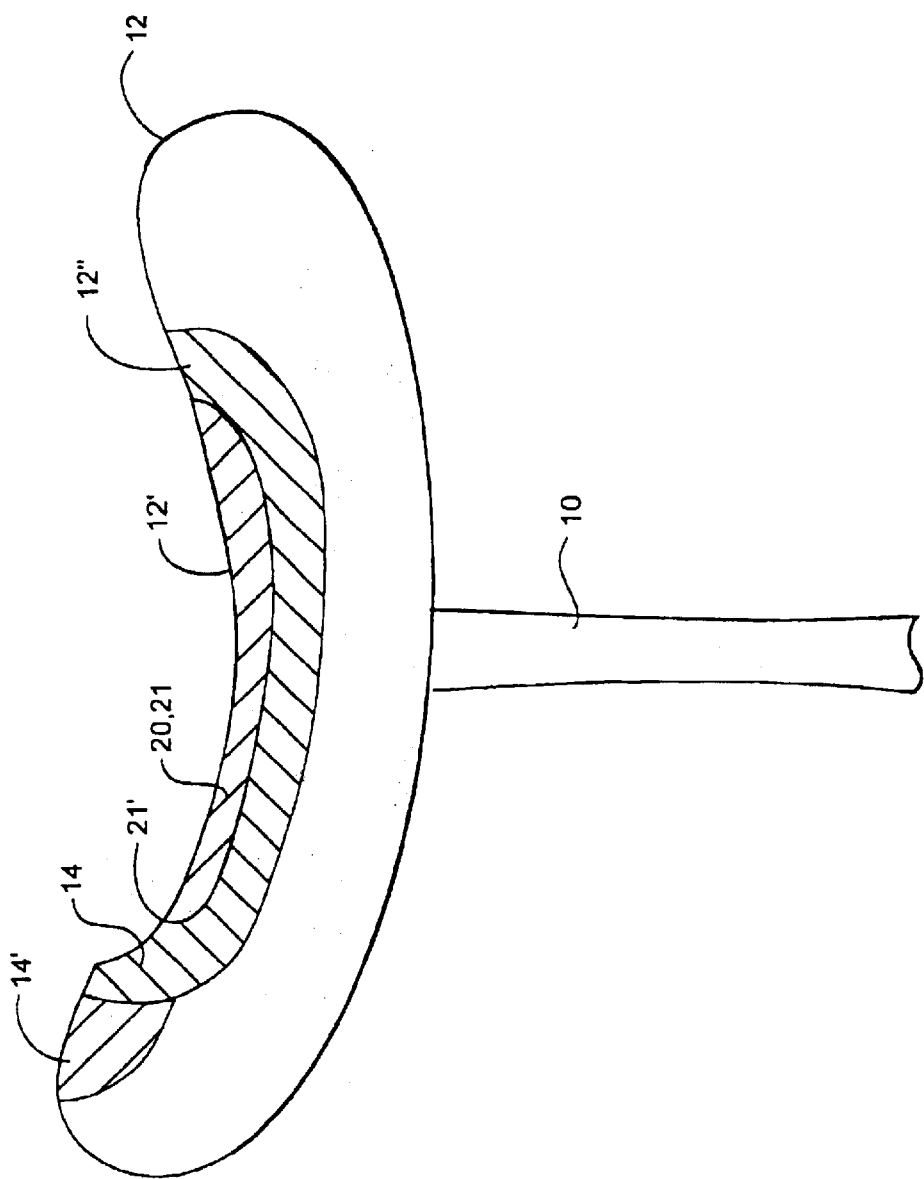
FIG. 21 is a lateral view illustrating the use of template with a conformable surface.

Referring now to FIG. 21, to eliminate these force concentrations and their effects, the shape and material selection, of template 12 can be configured to provide a cushioned or conformable template surface or layer 12' that is incorporated into the framework of template 12 and force application surface 14 (i.e., the conformable template surface will overlap the perimeter and encompass any internal supporting member). In a specific embodiment, the entire surface of template 12 and/or force application surface 14 is covered by a conformable layer 12' (similar to conformable layer 37) that is made of a semiconductive (for bipolar applications) or conductive (for monopolar applications) material that avoid enhanced pressure or electrical edge effects described herein. In another embodiment template 12 can have a laminated or layered construction whereby conformable layer 12' is joined or otherwise coupled to an inner rigid layer 12" (via adhesive bonding, ultrasonic welding or other joining method known in the art). Rigid layer 12 facilitated the in the transmission application of force 17 to tissue but does not contact tissue itself.

In various embodiments, conformable layer 12' can be constructed of conformable materials with similar properties as conformable layer 37. Materials with suitable conformable properties include various conformable polymers known in the art including, but not limited to polyurethanes, silicones and polytetrafluoroethylene. The polymer materials can be coated with conductive materials such as silver, silver chloride, and gold; or semiconductive coatings such as vapor-deposited germanium (described in US Pat. No. 5,373,305 which is incorporated by reference herein) using electro/vapor deposition or dip coating techniques, or constructed with semiconductive polymers such as metallophthalocyanines using polymer processing techniques known in the art. In various embodiments, the thickness and durometer of polymers used for force application surface 14 and/or RF electrode 18 can be further configured to: i) produce a uniform distribution of applied force across the electrode tissue interface 21 or ii) produce a gradient in stiffness and resulting applied force 17 across energy delivery surface 20.

In a preferred embodiment, force applications surface 14 and/or energy delivery surface 20 are configured to have maximum applied force 17 at their respective centers and decreasing applied force moving outward in the radial direction. In other embodiments, force application surface 14 can be engineered to produce varying force profiles or gradients at tissue interface 21 with respect to radial direction of template 12, force applications surface 14, or energy delivery surface 20. Possible force profiles include linear, stepped, curved, logarithmic with a minimum force at tissue interface edge 21' or force application edge 14' and increasing force moving in an inward radial direction. In a related embodiment, gradients in bending and compressive stiffness can be produced solely by varying the thickness of force application surface 14, electrode 18 or energy delivery surface 20 in their respective radial directions. In a preferred embodiment, force application surface 14 and/or electrode 18 has a maximum thickness and bending stiffness at their respective centers with a tapered decreasing thickness (and corresponding stiffness) moving out in their respective radial directions.

Figure 22:
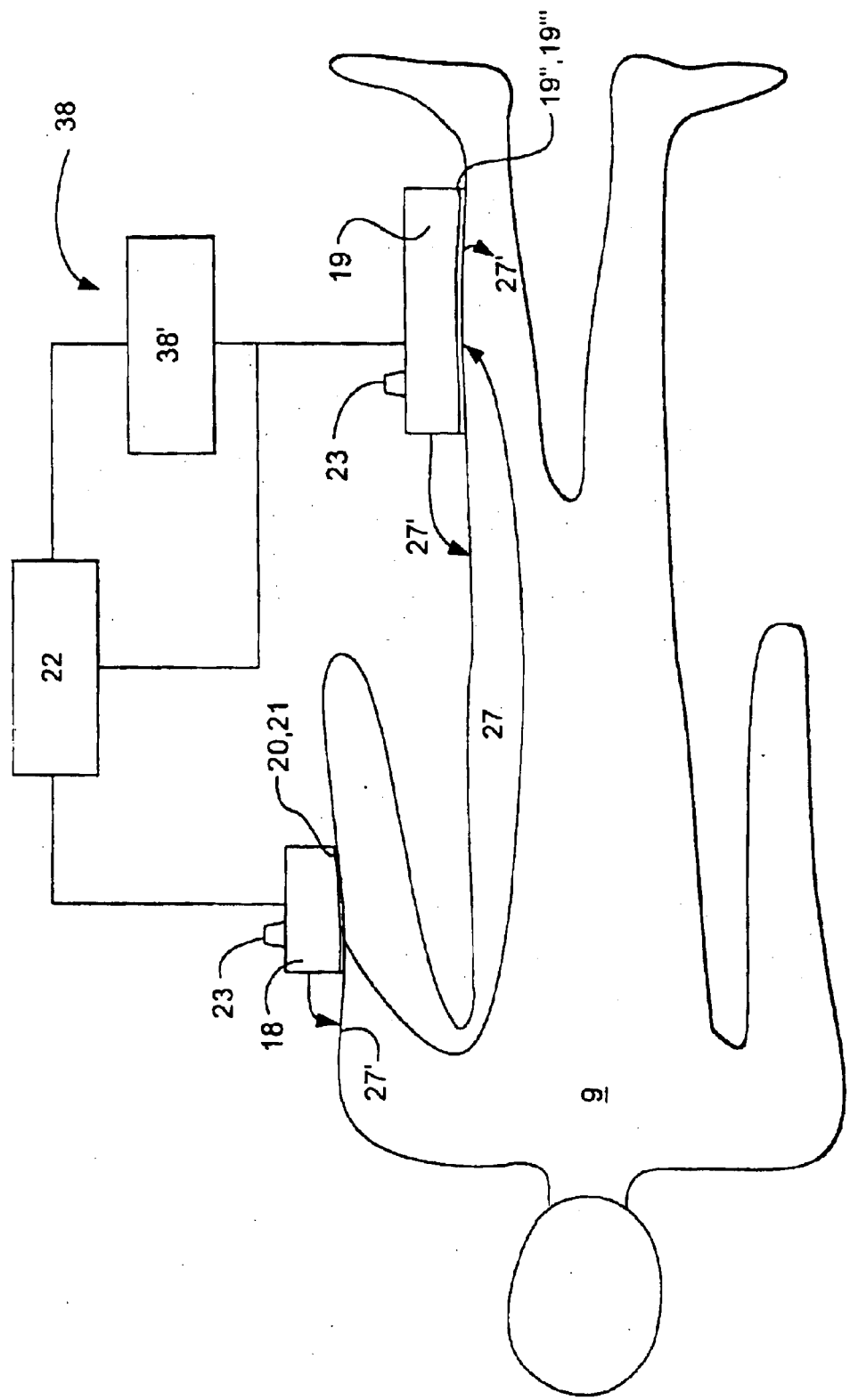
FIG. 22 is a schematic diagram illustrating the use of a monitoring system to monitor stray current from the active or the passive electrode.

In various embodiments, monitoring of both active electrode 18 and passive electrode 19 may be employed to prevent or minimize unwanted currents due to insulation breakdown, excessive capacitive coupling or current division. An active electrode monitoring system 38 shown in FIG. 22, uses a monitoring unit 38' to continuously monitor the level of stray current 27' flowing out of electrode 18 and interrupts the power should a dangerous level of leakage occur. Stray currents 27' include currents due to capacitive coupling and/or insulation failure of electrode 18. In various embodiments monitoring unit 38' can be integrated into or otherwise electronically coupled with a control system 54 and current monitoring circuitry described herein. Monitoring system 38 may also be configured to conduct stray current from the active electrode back to the RF generator and away from patient tissue. Monitoring unit 38' can comprise electronic control and measurement circuitry for monitoring impedance, voltage, current and temperature well known in the art. Unit 38' may also include a digital computer/microprocessors such as an application specific integrated circuit (ASIC) or a commercial microprocessor (such as the Intel7 Pentium7 series) with embedded monitoring and control software and input/output ports for electrical connections to sensors 23 and other measurement circuitry, to active electrode 18, passive electrode 19, RF generator 22 and other electrical connections including connections to the patient and ground. Monitoring unit 38' may also be incorporated into RF generator 22. In another embodiment monitoring system 38 is configured as a passive electrode monitoring system 39' that is used to monitor the passive electrode 19 and shut down current flow from RF generator 22 should the impedance of passive electrode 19 or interface 19' becomes too high or temperature at the interface 19' rise above a set threshold. In these embodiments passive electrode 19 is a split conductive surface electrode (known in the art) which can measure impedance at the interface 19' between patient tissue and the patient return electrode itself and avoid tissue burns. Prevention of pad burns is also facilitated by the coupling of temperature monitoring, impedance and/or contact sensors 23 (such as thermocouples or thermistor) to pad 19 and a monitoring unit 39' (which can be the same as monitoring unit 38' and likewise coupled to control system 54). Contact or impedance sensors 23 allows unit 39' to monitor the amount of electrical contact area 19''' of pad 19 that is in electrical contact with the skin and shut down or otherwise alarm should the amount of contact area fall below a minimum amount. Suitable contact sensors include pressure sensors, capacitance sensors, or resistors in suitable ranges and values known in the art for detecting electrical contact with the skin.

In one embodiment, elements of apparatus 8 is coupled to an open or closed loop feedback control system 54 (also called control system 54, control resources 54 and resources 54). Control system 54 is used to control the delivery of electromagnetic and mechanical energy to the skin surface and underlying soft tissue structure to minimize, and even eliminate, thermal damage to the skin and underlying tissue cell necrosis as well as blistering of the skin surface. Control system 54 also monitors other parameters including but not limited to, presence of an open circuit, short circuit or if voltage and current are supplied to the tissue for more than a predetermined maximum amount of time. Such conditions may indicate a problem with various components of apparatus 8 including RF generator 22, and monitoring unit 38' or 39'. Control system 54 can also be configure to control by deliver energy to selected tissue including epidermal, dermal, ans subdermal over a range of skin thermal conductivities including but not limited to the range 0.2 to 1.2 $W/(m^2 C.)$. In various embodiments, control system 54 can include a digital computer or microprocessors such as an application specific integrated circuit (ASIC) or a commercial microprocessor (such as the Intel® Pentium® series) with embedded monitoring and control software and input/output ports for electrical connections to sensors 23 and other measurement circuitry. In a related embodiment system 54 can comprise an energy control signal generator that generates an energy control signal.

Figure 23:
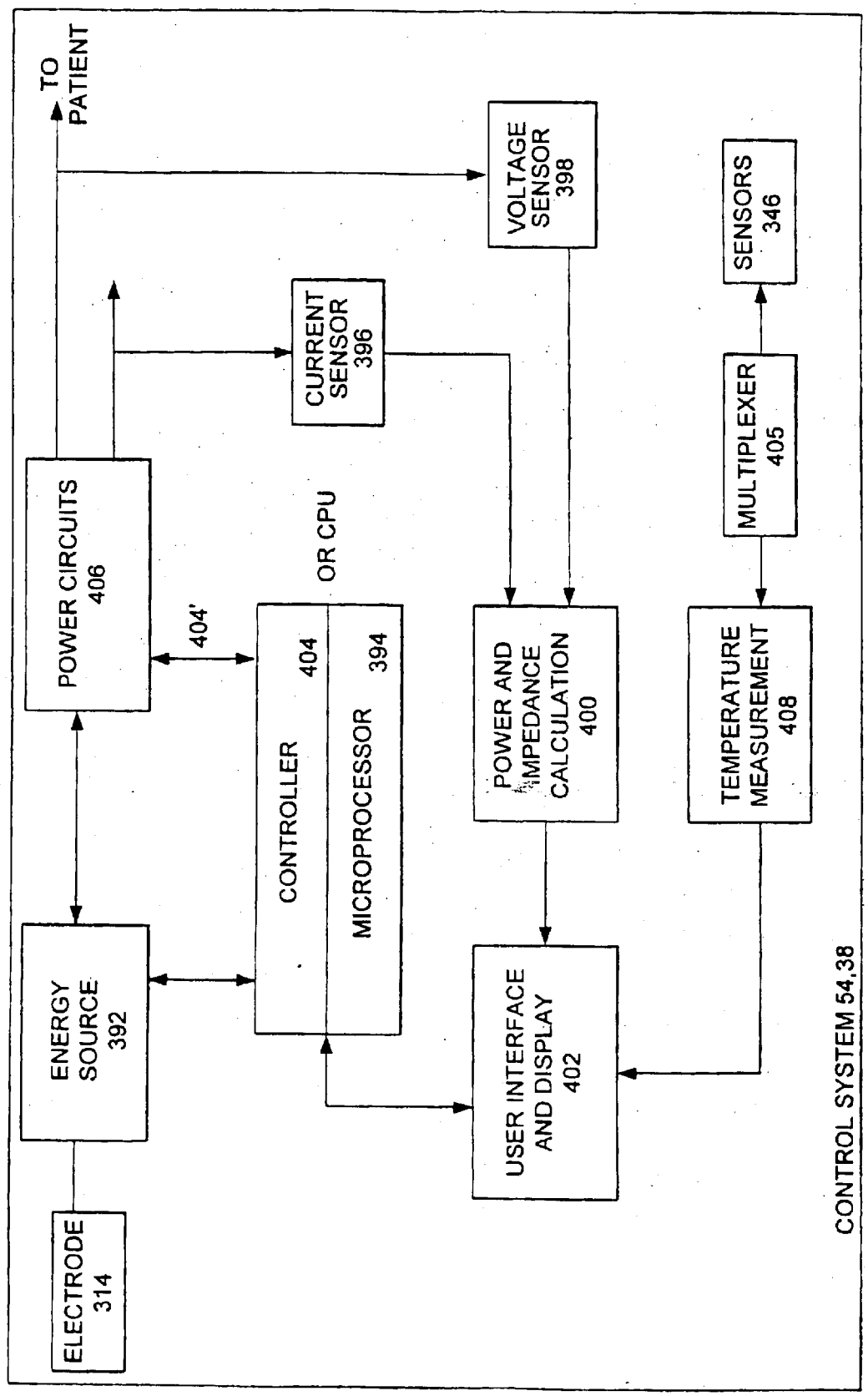
FIG. 23 depicts a block diagram of the feed back control system that can be used with the pelvic treatment apparatus.

Referring now to FIG. 23, an open or closed loop feedback control system 54 couples sensor 346 to energy source 392 (also called power source 392). In this embodiment, electrode 314 is one or more RF electrodes 314. The temperature of the tissue, or of RF electrode 314, is monitored, and the output power of energy source 392 adjusted accordingly. The physician can, if desired, override the closed or open loop control system 54. A microprocessor 394 can be included and incorporated in the closed or open loop system to switch power on and off, as well as modulate the power. Closed loop feedback control system 54 utilizes microprocessor 394 to serve as a controller, monitor the temperature, adjust the RF power, analyze the result, refeed the result, and then modulate the power.

With the use of sensor 346 and feedback control system 54, tissue adjacent to RF electrode 314 can be maintained at a desired temperature for a selected period of time without causing a shut down of the power circuit to electrode 314 due to the development of excessive electrical impedance at electrode 314 or adjacent tissue as is discussed herein. Each RF electrode 314 is connected to resources that generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404. A control signal 404' (also called energy control signal 404') is generated by controller 404 that is proportional to the difference between an actual measured value, and a desired value. The control signal is used by power circuits 406 to adjust the power output an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. A program memory and a data memory are also coupled to the bus. User interface and display 402 includes operator controls and a display. Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at each RF electrode 314 and also to monitor stray currents 427' (dues to insulation failure or capacitive coupling) flowing from electrode 314 The amount of RF energy delivered controls the amount of power. A profile of the power delivered to electrode 314 can be incorporated in controller 404 and a preset amount of energy to be delivered may also be profiled. Also, should stray current 427' rise to an undesired level, controller 404 shuts down power source 392.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 24:
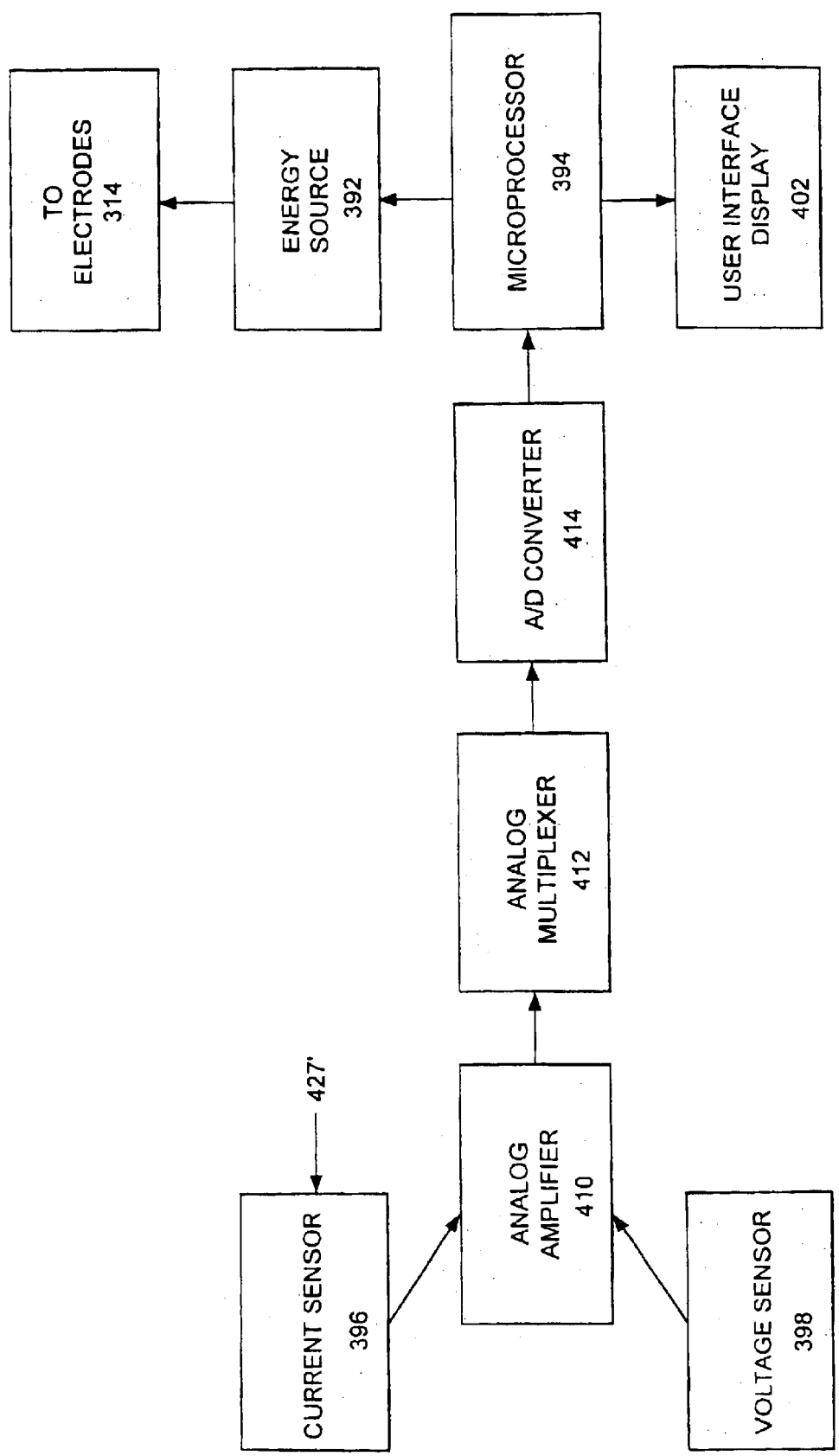
FIG. 24 depicts a block diagram of an analog amplifier, analog multiplexer and microprocessor used with the feedback control system of FIG. 23.

Referring now to FIG. 24, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage, which represents the respective sensed temperatures. Digitized amplifier output voltages are supplied by A/D converter 414 to microprocessor 394. Microprocessor 394 may be a MPC601 (PowerPC7) available from Motorola or a Pentium7 series microprocessor available from Intel7. In specific embodiments microprocessor 394 has a clock speed of 100 Mhz or faster and includes an on-board math-coprocessor. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances. Calculated power and impedance values can be indicated on user interface and display 402. Alternatively, or in addition to the numerical indication of power or impedance, calculated impedance and power values can be compared by microprocessor 394 to power and impedance limits. When the values exceed or fall below predetermined power or impedance values, a warning can be given on user interface and display 402, and additionally, the delivery of RF energy can be reduced, modified or interrupted. A control signal from microprocessor 394 can modify the power level supplied by energy source 392.

Figure 25:
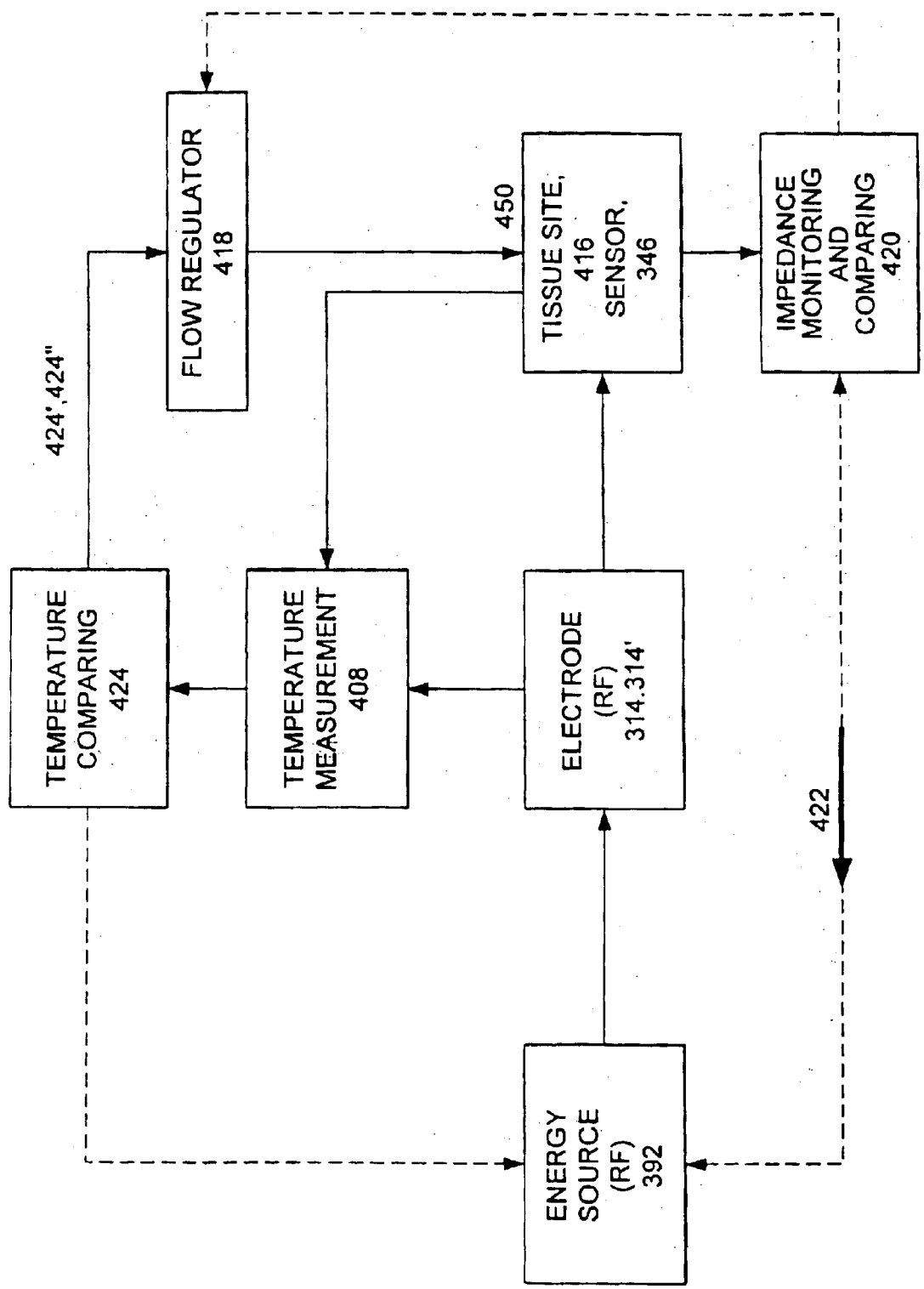
FIG. 25 depicts a block diagram of the operations performed in the feedback control system depicted in FIG. 23.

FIG. 25 illustrates a block diagram of a temperature and impedance feedback system that can be used to control the delivery of energy to tissue site 416 by energy source 392 and the delivery of cooling medium 450 to electrode 314 and/or tissue site 416 by flow regulator 418. Energy is delivered to RF electrode 314 by energy source 392, and applied to tissue site 416. A monitor 420 (also called impedance monitoring device 420) ascertains tissue impedance (at electrode 314, tissue site 416 or a passive electrode 314'), based on the energy delivered to tissue, and compares the measured impedance value to a set value. If measured impedance is within acceptable limits, energy continues to be applied to the tissue. However if the measured impedance exceeds the set value, a disabling signal 422 is transmitted to energy source 392, ceasing further delivery of energy to RF electrode 314. The use of impedance monitoring with control system 54 provides a controlled delivery of energy to tissue site 416 (also called mucosal layer 416) and underlying cervical soft tissue structure which reduces, and even eliminates, cell necrosis and other thermal damage to mucosal layer 416. Impedance monitoring device 420 is also used to monitor other conditions and parameters including, but not limited to, presence of an open circuit, short circuit; or if the current/energy delivery to the tissue has exceeded a predetermined time threshold. Such conditions may indicate a problem with apparatus 24. Open circuits are detected when impedance falls below a set value, while short circuits and exceeded power delivery times are detected when impedance exceeds a set value.

The control of cooling medium 450 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the measured temperature has not exceeded the desired temperature, comparator 424 sends a signal 424' to flow regulator 418 to maintain the cooling solution flow rate at its existing level. However if the tissue temperature is too high, comparator 424 sends a signal 424" to a flow regulator 418 (connected to an electronically controlled micropump, not shown) representing a need for an increased cooling medium 450 flow rate.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A treatment apparatus, comprising:
   an energy delivery device including at least a light energy member an RF energy member, and at least one energy delivery surface, the at least one energy delivery surface configured to deliver energy from the light energy member and the RF energy member to and through a skin surface and create a tissue effect at the skin surface or at a tissue below the skin surface; and
   a cooling member coupled to the energy delivery device.

2. The apparatus of claim 1, further comprising:
   a feedback control coupled to at least one of the cooling member, the light energy member or the RF energy member.

3. The apparatus of claim 1, wherein the cooling member is configured to deliver a controllable amount of cooling fluidic medium.

4. The apparatus of claim 1, wherein the cooling member is configured to cool at least a portion of the at least one energy delivery surface.

5. The apparatus of claim 1, wherein the at least one energy delivery surface is non-planar.

6. The apparatus of claim 1, wherein a fluid or gel is positioned between the skin surface and the at least one energy delivery surface.

7. The apparatus of claim 1, wherein the at least one energy delivery surface is a solid surface.

8. The apparatus of claim 1, wherein the at least one energy delivery surface includes a first section and a second section.

9. The apparatus of claim 1, wherein the first section and the second section are non-planar.

10. The apparatus of claim 9 wherein the first section is a surface of the RF energy member and the second section is a surface of the light energy member.

11. The apparatus of claim 9, wherein the RF energy member is a pair of bi-polar RF electrodes.

12. A treatment apparatus, comprising:
    an energy delivery device including an energy delivery surface;
    at least a first and a second energy delivery member coupled to the energy delivery device, the first and second energy delivery members delivering different types of energy; and
    a cooling member coupled to the energy delivery device, wherein the cooling member is configured to evaporatively cool a back surface of the energy delivery surface and conductively cool a tissue site.

13. A treatment apparatus, comprising:
    an assembly;
    an energy delivery device coupled to the assembly, the energy delivery device including at least a light energy member, an RF energy member, and at least one energy delivery surface, the at least one energy delivery surface configured to deliver energy from the light energy member and the RF energy member to and through a skin surface and create a tissue effect at the skin surface or at a tissue below the skin surface;
    a cooling member coupled to the assembly and configured to provide cooling to at least a tissue surface; and
    an electronic control device configured to facilitate operation of at least one of the light energy member or the RF energy member.

14. The apparatus of claim 13 further comprising:
    a second RF energy member coupled to the assembly.

15. The apparatus of claim 13, wherein the first and second RF energy members are bipolar electrodes.

16. The apparatus of claim 13, further comprising:
    a feedback control coupled to at least one of the cooling member, the RF energy member and the light energy member.

17. The apparatus of claim 13, wherein the cooling member is configured to deliver a controllable amount of cooling fluidic medium to at least one of the light energy member or the RF energy member.

18. The apparatus of claim 13, wherein cooling member is configured to cool the energy delivery surface.

19. The apparatus of claim 13, wherein the cooling member utilizes fluid to cool the RF energy member and conductively cool a skin surface in thermal contact with the at least one energy delivery surface.

20. A treatment apparatus, comprising:
    an assembly including at least one energy delivery surface;
    an electromagnetic energy device coupled to the assembly, the electromagnetic energy device including at least a light energy member and an RF energy member, the at least one energy delivery surface configured to deliver energy from the light energy member and the RF energy member to and through a skin surface and create a tissue effect at the skin surface or at a tissue below the skin surface;
    a cooling member coupled to the assembly and configured to provide cooling to at least a portion of the at least one energy delivery surface; and
    an electronic control device configured to facilitate operation of at least one of the light energy member or the RF energy member.

21. A treatment apparatus, comprising:
    an energy delivery device including an energy delivery surface made at least partially of a material that transmits light;
    an electromagnetic energy device including at least a first RF electrode and a light delivery device coupled to the device; and
    a cooling member coupled to the device.

22. The apparatus of claim 21, further comprising:
    a second RF electrode.

23. The apparatus of claim 22, wherein the first and second RF electrodes are bipolar electrodes.

24. The apparatus of claim 21, further comprising:
    an electronic control device configured to facilitate operation of at least one of the first RF electrode, the cooling member and the light delivery device.

25. The apparatus of claim 21, further comprising:
    a sensor coupled to at least one of the first RE electrode, the cooling member and the light delivery device.

26. The apparatus of claim 21, further comprising:
    a light energy source coupled to the light delivery device.

27. The apparatus of claim 26, wherein the light energy source is a coherent light source.

28. The apparatus of claim 26, wherein the light energy source is an incoherent light source.

29. The apparatus of claim 21, further comprising:
    an RF generator coupled to the first RF electrode.

30. A treatment apparatus, comprising:
    an energy delivery device including an energy delivery surface;
    a pair of bi-polar RF electrodes coupled to the energy delivery surface;

a light delivery device coupled to the device and positioned to transmit light through the energy delivery surface.

31. The apparatus of claim 30, further comprising:
an electronic control device configured to facilitate operation of at least one of the pair of bi-polar RF electrodes, the cooling member and the light delivery device.

32. The apparatus of claim 30, further comprising:
a sensor coupled to at least one of the RF electrode, the cooling member and the light delivery device.

33. The apparatus of claim 30, further comprising:
a light energy source coupled to the light delivery device.

34. The apparatus of claim 30, wherein the light energy source is a coherent light source.

35. The apparatus of claim 30, wherein the light energy source is an incoherent light source.

36. The apparatus of claim 30, further comprising:
an RF generator coupled to the RF electrode.

37. A method for inducing the formation of collagen in a selected collagen containing tissue site beneath a skin surface, comprising:
providing an energy source;
producing energy from the energy source;
cooling through the skin surface, wherein a temperature of the skin surface is lower than the selected collagen containing tissue site; and
delivering energy from the energy source through the skin surface to the selected collagen containing tissue site for a sufficient time to induce collagen formation in the selected collagen containing tissue site, and forming no more than a second degree burn of the skin, wherein the energy is delivered in an amount not exeeding 600 joules/cm2 during a single treatment session;
and creating a tissue effect.

38. A method for inducing the formation of collagen in a selected collagen containing tissue site beneath a skin surface, comprising:
providing an energy source;
producing energy from the energy source;
delivering energy from the energy source through the skin surface to the selected collagen containing tissue site for a sufficient time to induce a formation of new collagen in the selected collagen containing tissue site and forming no more than a second degree burn of the skin, wherein the energy is delivered in an amount that does not exceed 1,000 joules/cm2 at the skin surface; and
creating a tissue effect.

39. A method for inducing the formation of collagen in a selected a collagen containing tissue site beneath a skin surface, comprising:
providing an energy source;
delivering energy to the skin and operating in a range of skin thermal conductivities at or near the conductivity of the skin of 0.20 to 1.2 W/(meter° C.);
cooling the skin surface, wherein a temperature of the skin surface is lower than the collagen containing tissue site; and
forming new collagen in the selected collagen containing tissue site with no more than a second degree burn of the skin; and
creating a tissue effect.

40. A method of creating a tissue effect, comprising:
providing a treatment apparatus that includes at least a first RF electrode;
cooling the skin surface, wherein a temperature of the skin surface is lower than tissue underlying the skin surface; and
delivering energy from the treatment apparatus through the skin surface to the tissue underlying the skin surface for a sufficient time to create a desired tissue effect with no more than a second degree burn formed of the skin surface.

41. The method of claims 37, 39 or 40, wherein the treatment apparatus includes a light delivery device.

42. The method of claims 37, 39 or 40, wherein the tissue effect is dermal remodeling.

43. The method of claims 37, 39 or 40, wherein the tissue effect is skin tightening.

44. The method of claims 37, 39 or 40, wherein the tissue effect is wrinkle reduction.

45. The method of claims 37, 39 or 40, wherein the tissue effect is elastosis reduction.

46. The method of claims 37, 39 or 40, wherein the tissue effect is scar reduction.

47. The method of claims 37, 39 or 40, wherein the tissue effect is hair follicle modification.

48. The method of claims 37, 39 or 40, wherein the tissue effect is modification of contour irregularities of a skin surface.

49. The method of claims 37, 39 or 40, wherein the tissue effect is a creation of scar or nascent collagen.

50. A method of creating a tissue effect, comprising:
providing a treatment apparatus that includes at least a first electromagnetic energy delivery device;
cooling through a skin surface, wherein a temperature of the skin surface is lower than tissue underlying the skin surface; and
delivering energy from the treatment apparatus through a skin surface to a selected collagen containing tissue site for a sufficient time to induce a formation of new collagen in the selected collagen containing tissue site with no more than a second degree burn of the skin wherein the energy is delivered in an amount that does not exceed 1,000 joules/cm2 at the skin surface;
modifying at least a portion of the skin surface.

51. The method of claim 50, wherein the treatment apparatus includes a light delivery device coupled to a device.

52. A method for creating a tissue effect, comprising:
providing a treatment apparatus that includes an energy delivery surface and at least a first RF electrode;
coupling the energy delivery surface with an external surface of the skin;
cooling a surface of the skin while heating underlying collagen containing tissue, wherein a temperature of the skin surface is lower than a temperature of the underlying collagen containing tissue;
delivering energy from the treatment apparatus through the skin surface to a selected collagen containing tissue site for a sufficient time to induce a formation of new collagen in the selected collagen containing tissue site with no more than a second degree burn of the skin; and
creating a desired tissue effect.

53. The method of claim 52, wherein the treatment apparatus includes a light delivery device.

54. A method of creating a tissue effect, comprising:
providing a treatment apparatus that includes an energy delivery surface and at least a first RF electrode, wherein the energy is delivered in an amount not exceeding 600 joules/cm2 during a single treatment session;

reducing a temperature of a collagen containing tissue site below a temperature of a skin surface, creating a thermal injury to at least a portion of the collagen in the collagen containing tissue site with a minimal cellular destruction in the epidermis; and inducing collagen formation.

55. The method of claim 54, wherein the treatment apparatus includes a light delivery device.

56. A method of creating a tissue effect, comprising:

providing a treatment apparatus that includes an energy delivery surface and at least a first RF electrode;

coupling the energy delivery surface with a skin surface;

cooling through the skin surface, wherein a temperature of the skin surface is lower than a temperature of an underlying collagen containing tissue;

delivering energy from the treatment apparatus through the skin surface to the underlying collagen containing tissue for a sufficient time to induce collagen formation.

57. The method of claim 56, wherein the treatment apparatus includes a light delivery device.

58. A treatment apparatus, comprising:

a device;

an energy delivery device coupled to the device, the energy delivery device including at least a light energy member, an RF energy member, and at least one energy delivery surface, the at least one energy delivery surface configured to deliver energy from the light energy member and the RF energy member to and through a skin surface and create a tissue effect at the skin surface or at a tissue below the skin surface; and a cooling member coupled to the device.

59. A treatment apparatus, comprising:

an assembly;

an energy delivery device coupled to the assembly, the energy delivery device including at least a light energy member, an RF energy member, and at least one energy delivery surface, the at least one energy delivery surface configured to deliver energy from the light energy member and the RF energy member to and through a skin surface and create a tissue effect at the skin surface or at a tissue below the skin surface;

a cooling member coupled to the assembly and configured to provide cooling at the skin surface; and an electronic control device configured to facilitate operation of at least one of the light energy member or the RF energy member.

60. A method for inducing the formation of collagen in a selected collagen containing tissue site beneath a skin surface, comprising:

delivering electromagnetic energy from an electromagnetic energy delivery device and operating in a range of skin thermal conductivities at or near the conductivity of the skin of 0.20 to 1.2 W/(meter° C.);

cooling the skin surface, wherein a temperature of the skin surface is lower than the selected collagen containing tissue site; and delivering energy from the energy source through the skin surface to the selected collagen containing tissue site for a sufficient time to induce collagen formation in the selected collagen containing tissue site with no more than a second degree burn of the skin; and creating a tissue effect.

61. A method of creating a tissue effect, comprising:

providing an electromagnetic energy delivery device;

cooling a skin surface, wherein a temperature of the skin epidermis surface is lower than tissue underlying the skin surface; and delivering energy from the electromagnetic energy delivery device through the skin surface to the tissue underlying the skin surface for a sufficient time to create a desired tissue effect with no more than a seond degree burn formed of the skin, wherein the energy is delivered in an amount not exceeding 600 joules/cm2 during a single treatment session.

62. The method of claim 61, wherein the tissue effect is dermal remodeling.

63. The method of claim 61, wherein the tissue effect is skin tightening.

64. The method of claim 61, wherein the tissue effect is wrinkle reduction.

65. The method of claim 61, wherein the tissue effect is elastosis reduction.

66. The method of claim 61, wherein the tissue effect is scar reduction.

67. The method of claim 61, wherein the tissue effect is hair follicle modification.

68. The method of claim 61, wherein the tissue effect is modification of contour irregularities of a skin surface.

69. The method of claim 61, wherein the tissue effect is a creation of scar or nascent collagen.

70. A method of creating a tissue effect, comprising:

providing a treatment apparatus that includes at an electromagnetic energy delivery device;

cooling through a skin surface, wherein a temperature of the skin epidermis surface is lower than tissue underlying the skin surface;

delivering energy from the electromagnetic energy delivery device through a skin surface to a selected collagen containing tissue site of the tissue underlying the skin surface for a sufficient time to induce a formation of new collagen in the selected collagen containing tissue site with no more than a second degree burn formed of the skin, wherein the energy is delivered in an amount that does not exceed 1,000 joules/cm2 at the skin surface; and modifying at least a portion of the skin surface.

71. A method of creating a tissue effect, comprising:

providing a treatment apparatus that includes an electromagnetic energy delivery device and operating in a range of skin thermal conductivities at or near the conductivity of the skin of 0.20 to 1.2 W/(meter° C.):

reducing a temperature of a collagen containing tissue side below a temperature of a skin surface, creating a thermal injury to at least a portion of the collagen in the collagen containing tissue site with no more than a second degree burn created of the skin; and inducing collagen formation.

* * * * *